(12) United States Patent
Tanaka

(10) Patent No.: US 11,317,792 B2
(45) Date of Patent: May 3, 2022

(54) FIXING UNIT OF LIGHT GUIDE MEMBER, ILLUMINATION APPARATUS, AND ENDOSCOPE

(71) Applicant: Olympus Corporation, Hachioji (JP)

(72) Inventor: Yoshinori Tanaka, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 578 days.

(21) Appl. No.: 16/280,383

(22) Filed: Feb. 20, 2019

(65) Prior Publication Data

US 2019/0175005 A1 Jun. 13, 2019

Related U.S. Application Data

(63) Continuation of application No. PCT/JP2016/075984, filed on Sep. 5, 2016.

(51) Int. Cl.
*A61B 1/00* (2006.01)
*A61B 1/06* (2006.01)
(Continued)

(52) U.S. Cl.
CPC .......... *A61B 1/0669* (2013.01); *A61B 1/0011* (2013.01); *A61B 1/00096* (2013.01);
(Continued)

(58) Field of Classification Search
None
See application file for complete search history.

(56) References Cited

U.S. PATENT DOCUMENTS 6,142,930 A * 11/2000 Ito ...................... A61B 1/00096
348/76
2012/0136212 A1 5/2012 Komukai et al.
(Continued)

FOREIGN PATENT DOCUMENTS

JP 05-333218 12/1993
JP 2002-243997 8/2002
(Continued)

OTHER PUBLICATIONS

International Search Report and Written Opinion from corresponding International Application No. PCT/JP2016/075984, dated Nov. 29, 2016.

*Primary Examiner* — Timothy J Neal
(74) *Attorney, Agent, or Firm* — Scully, Scott, Murphy & Presser, P.C.

(57) ABSTRACT

The disclosed technology is directed to a fixing unit of a light guide member. The fixing unit is attaching the light guide member to a protective member that protects outer circumference of the light guide member that guides primary light and a holding member. The fixing unit comprises a defining member forming a spatial region in which the protective member and the holding member are encapsulated separately from one another in a longitudinal axis direction of the fixing unit. An adhesive that is applied in the spatial region to bond at least part of the protective member and at least part of the holding member to the defining member. The defining member includes a specific region that defines a bonding range of the adhesive in the spatial region in at least one of a longitudinal axis direction and a radial direction of the defining member.

19 Claims, 11 Drawing Sheets

(51) Int. Cl.
  *G02B 23/24* (2006.01)
  *A61B 1/07* (2006.01)
  *G02B 6/42* (2006.01)

(52) U.S. Cl.
  CPC ...... *A61B 1/00126* (2013.01); *A61B 1/00165* (2013.01); *A61B 1/07* (2013.01); *G02B 23/2469* (2013.01); *G02B 6/4298* (2013.01)

(56) References Cited

U.S. PATENT DOCUMENTS

2013/0329026 A1\* 12/2013 Hida ................ A61B 1/04
  348/65
2015/0238069 A1\* 8/2015 Osada ................ G02B 23/2423
  600/109

FOREIGN PATENT DOCUMENTS

| JP | 2012-115420 | 6/2012 |
| JP | 5484303 | 2/2014 |
| JP | 2014-180458 | 9/2014 |

\* cited by examiner

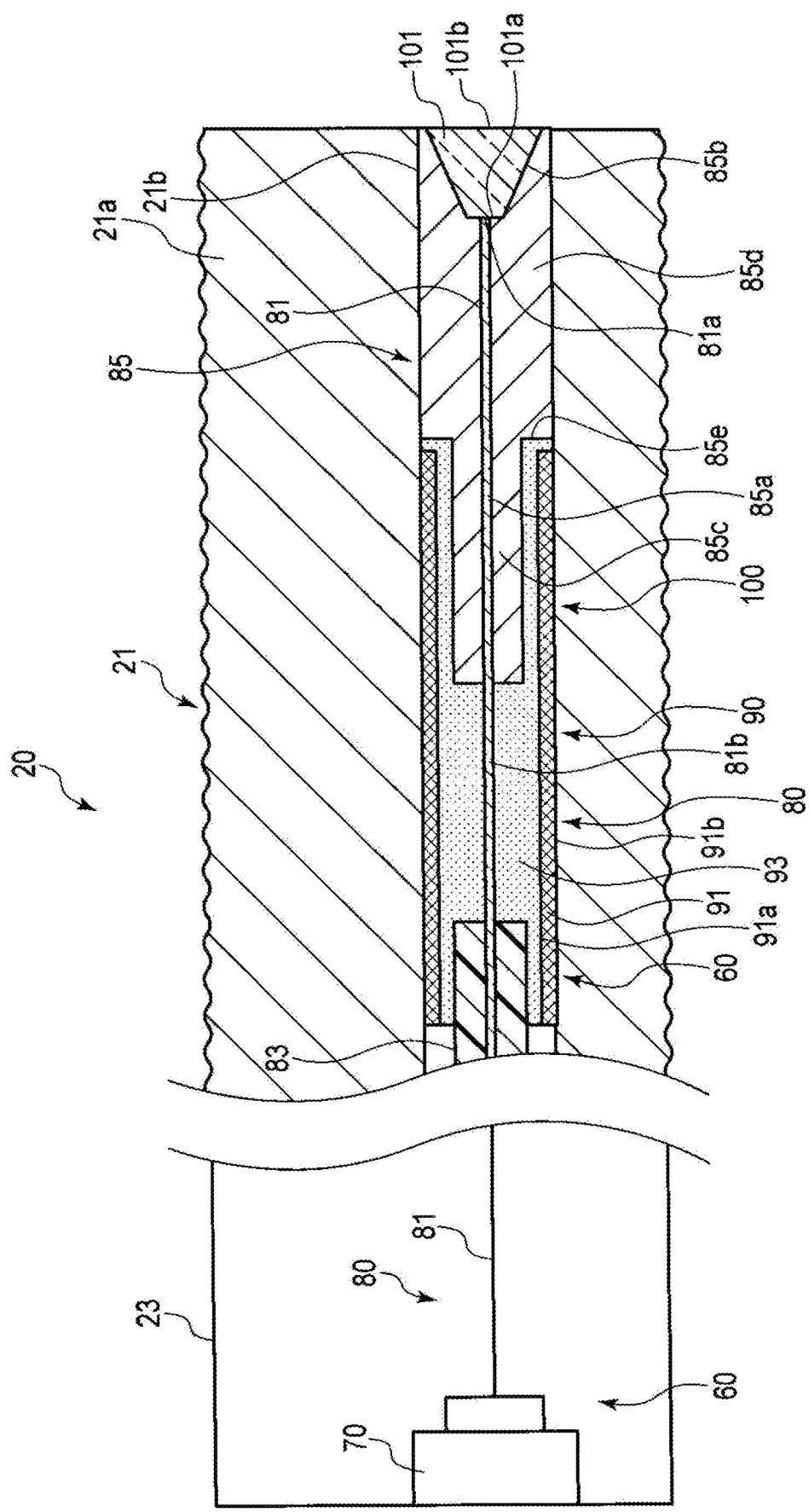

FIXING UNIT OF LIGHT GUIDE MEMBER, ILLUMINATION APPARATUS, AND ENDOSCOPE

CROSS-REFERENCE TO RELATED APPLICATION

This application is a continuation application of PCT Application No. PCT/JP2016/075984 filed on Sep. 5, 2016, which is hereby incorporated by reference in its entirety.

TECHNICAL FIELD

The disclosed technology relates to a fixing unit of a light guide member, illumination apparatus, and an endoscope.

DESCRIPTION OF THE RELATED ART

For example, an illumination optical system unit for an endoscope disclosed in Japanese Patent No. 5484303 has an optical fiber, a phosphor optically connected to an end portion of the optical fiber, and a protective cover that covers the distal surface side of the phosphor. Furthermore, the illumination optical system unit for an endoscope has a sleeve member that covers the outer circumference of the phosphor and has a receiving portion that holds the protective cover at the distal end. Plural circumferential grooves are formed in the receiving portion of the sleeve member and each of the circumferential grooves is disposed in a concentric circular manner. For sealing at the distal end of the sleeve member, a first adhesive is poured into between the receiving portion and the protective cover and into the circumferential grooves. The first adhesive is controlled to an appropriate amount by the circumferential grooves.

The illumination optical system unit for an endoscope disclosed in Japanese Patent No. 5484303 further has a ferrule that holds the end portion of the optical fiber and the phosphor and a cylindrical protective tube that protects the optical fiber protruding from the ferrule to the external toward the opposite side to the phosphor. The ferrule engages with a hole of the sleeve member and the proximal portion of the ferrule protrudes from the hole to the external. The protective tube covers the outer circumferential surface of the sleeve member and the outer circumferential surface of the proximal portion of the ferrule and is bonded to these outer circumferential surfaces by a second adhesive. For filling of the gap between the inner circumferential surface of the protective tube and the outer circumferential surfaces of the sleeve member and the ferrule with the second adhesive, the inner diameter dimension of the protective tube is allowed to have room so as to be larger than the outer diameter dimension of the sleeve member and the outer diameter dimension of the ferrule.

Due to the room of the protective tube, the second adhesive runs over from the protective tube to the external, in other words, runs over to the outer circumferential surfaces of the sleeve member and the ferrule, in some cases. The amount of running-over varies every bonding. Therefore, the bonding range of the second adhesive is not defined every bonding.

In general, the illumination optical system unit for an endoscope is engaged with an illumination hole of a distal hard portion that is a distal holding portion incorporated in the distal portion of an insertion portion of the endoscope. The inner circumferential shape and size of the illumination hole are defined in advance and do not get deformed. Therefore, if the bonding range of the second adhesive is not defined in at least one of the longitudinal axis direction and the radial direction of the illumination optical system unit for an endoscope, the adhesive gets caught on the illumination hole in some cases. In this case, the illumination optical system unit for an endoscope that cannot be inserted into the illumination hole due to the catching is caused and the endoscope cannot be assembled in some cases.

Furthermore, if the bonding range of the second adhesive is not defined, the strength of the illumination optical system unit for an endoscope including the second adhesive is not ensured in some cases.

Accordingly, there is a need for a fixing unit of a light guide member, illumination apparatus, and an endoscope that can define the bonding range of an adhesive and ensure the strength of a unit including the adhesive.

BRIEF SUMMARY OF EMBODIMENTS

In order to achieve the object described hereinbefore, a fixing unit of a light guide member relating to one aspect of the disclosed technology is a fixing unit of a light guide member that fixes the light guide member to a protective member that protects outer circumference of the light guide member that guides primary light and a holding member that holds an end portion of the light guide member that protrudes from the protective member. The fixing unit has a defining member having a spatial region in which the protective member and the holding member are disposed in the state of being separated from each other in a longitudinal axis direction of the fixing unit and an adhesive that is disposed in the spatial region and bonds at least part of the protective member and at least part of the holding member to the defining member. The defining member defines a bonding range of the adhesive in at least one of a longitudinal axis direction and a radial direction of the defining member.

In order to achieve the object described hereinbefore, illumination apparatus relating to one aspect of the disclosed technology includes a light source portion that emits primary light and an illumination unit that converts an optical characteristic of at least part of the primary light emitted from the light source portion to generate secondary light and emit the generated secondary light to the external as illumination light. The illumination unit has a light guide member that guides the primary light emitted from the light source portion, a protective member that protects outer circumference of the light guide member, a holding member that holds an end portion of the light guide member that protrudes from the protective member, and the fixing unit that is described hereinbefore and fixes the protective member and the holding member to each other in the state in which the protective member and the holding member are separated from each other in a longitudinal axis direction of the fixing unit.

In order to achieve the object described hereinbefore, an endoscope relating to one aspect of the disclosed technology includes the illumination apparatus described hereinbefore.

According to the disclosed technology, it is possible to provide a fixing unit of a light guide member, illumination apparatus, and an endoscope that can define the bonding range of an adhesive and ensure the strength of a unit including the adhesive.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 2 is a schematic diagram of illumination apparatus according to the first embodiment and is a diagram depicting that a fixing unit is applied to an illumination portion of the illumination apparatus.

DETAILED DESCRIPTION OF THE EMBODIMENTS

Figure 1:
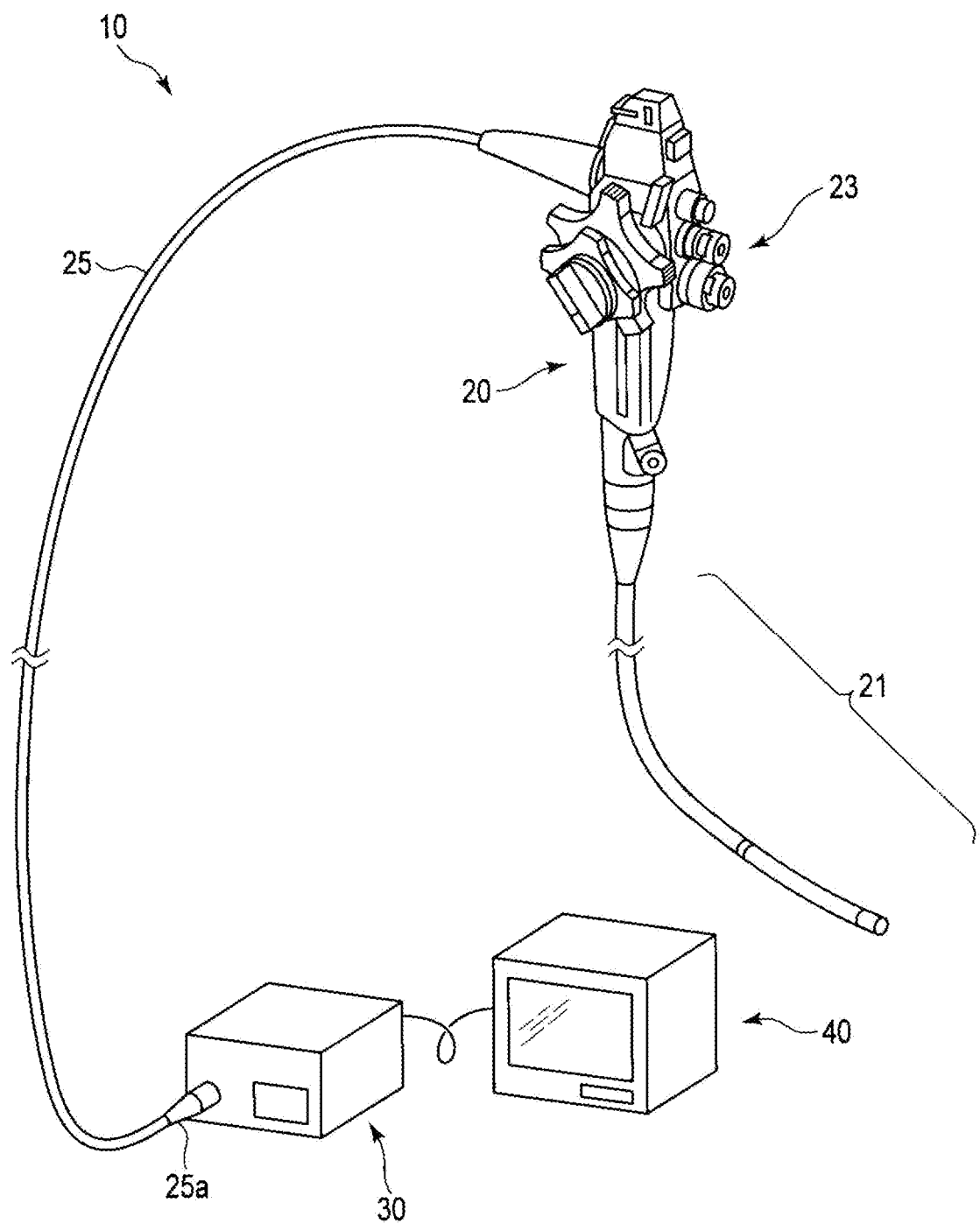
FIG. 1 is a schematic diagram of an endoscope system according to a first embodiment of the disclosed technology.

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Embodiments of the disclosed technology will be described below with reference to the drawings. In part of the drawings, diagrammatic representation of part of components is omitted for clarification of the diagrammatic representation. Description will be made by taking as one example the case in which illumination apparatus 60 depicted in FIG. 2 is illumination apparatus for an endoscope mounted in an endoscope 20 of an endoscope system 10 depicted in FIG. 1, for example. The illumination apparatus 60 may be mounted in equipment other than the endoscope 20, e.g. a microscope, or may function as apparatus alone. In the longitudinal axis direction of the illumination apparatus 60, which is the right-left direction of FIG. 2, the side of a light source 70, or a light source portion 70 will be referred to as the rear side and the side of an optical element 101 will be referred to as the front side.

First Embodiment

A first embodiment of the disclosed technology will be described hereinafter.

The endoscope system 10 like that depicted in FIG. 1 is set in an inspecting room, operating room, or the like, for example. The endoscope system 10 has the endoscope 20 that images the inside of a conduit portion such as a lumen of a patient, for example, and control apparatus 30 having an image processing portion that is not depicted in the diagram and executes image processing of an image of the inside of the conduit portion imaged by an imaging unit that is not depicted in the diagram in the endoscope 20. The endoscope system 10 further has display apparatus 40 that is connected to the control apparatus 30 and displays the image resulting from the image processing by the image processing portion.

The endoscope 20 functions as insertion equipment inserted into a conduit portion, for example. The endoscope 20 may be a forward-viewing endoscope and may be a side-viewing endoscope.

The endoscope 20 of the present embodiment will be described as the endoscope 20 for medical use, for example, but does not need to be limited thereto. The endoscope 20 may be an endoscope for industrial use inserted into a conduit portion of an industrial product such as a pipe or may be an insertion instrument such as a catheter, for example, having only the illumination apparatus 60.

As depicted in FIG. 1, the endoscope 20 has a hollow, elongated insertion portion 21 inserted into a conduit portion and an operation portion 23 that is joined to the proximal portion of the insertion portion 21 and operates the endoscope 20. The endoscope 20 has a universal cord 25 that is connected to the operation portion 23 and is extended from a side surface of the operation portion 23.

The insertion portion 21 has an imaging element of the imaging unit, which is not depicted in the diagram. The imaging element is set at the distal portion of the insertion portion 21. The imaging element images reflected light from a subject illuminated by illumination light emitted from the optical element 101 to be described hereinafter and outputs the reflected light as an electrical signal to the image processing portion. The imaging element has a charge coupled device (CCD), for example. The image processing portion is formed of a hardware circuit including an application specific integrated circuit (ASIC) and so forth, for example.

As depicted in FIG. 1, the universal cord 25 has a connecting portion 25a that can be attached to and detached from the control apparatus 30. The connecting portion 25a allows the endoscope 20 and the control apparatus 30 to be connected to each other attachably/detachably. The connecting portion 25a is installed for transmission and reception of data between the endoscope 20 and the control apparatus 30.

In the endoscope system 10, the endoscope 20 is directly connected to the control apparatus 30 via the universal cord 25 including the connecting portion 25a. However, the universal cord 25 may be omitted and the endoscope 20 may be a wireless-type endoscope although diagrammatic representation is not made. In this case, the endoscope 20 is connected to the control apparatus 30 by wireless signals.

As depicted in FIG. 2, the endoscope 20 has the illumination apparatus 60 that emits the illumination light to the external of the endoscope 20. The illumination apparatus 60 has the light source portion 70 that emits primary light and an illumination unit 80 optically connected to the light source portion 70. The illumination unit 80 converts optical characteristics of at least part of the primary light emitted from the light source portion 70 to generate secondary light. The illumination unit 80 emits the generated secondary light to the external of the endoscope 20 as the illumination light.

The light source portion 70 is mounted inside the operation portion 23, for example. The light source portion 70 has a light source that emits the primary light having high coherence and is not depicted in the diagram. Such a light source is a laser diode that emits laser light and is not depicted in the diagram, for example. The color of the laser light is blue, for example. The center wavelength of the blue laser light is 445 nm, for example. The center wavelength of the laser light does not need to be limited thereto. The light source portion 70 has a lens that is disposed on the front side of the laser diode and is not depicted in the diagram. The light source portion 70 has a receptacle that is not depicted in the diagram and to which a light guide member 81 to be described hereinafter in the illumination unit 80 is optically connected. This component to which the light guide member 81 is optically connected is not limited to the receptacle and may be a pigtail. The light source portion 70 may be incorporated in the control apparatus 30, for example. Therefore, the illumination apparatus 60 may be mounted in the endoscope system 10 and the mounting position of the illumination apparatus 60 is not particularly limited.

As depicted in FIG. 2, the illumination unit 80 has the light guide member 81 that guides the primary light emitted from the light source portion 70 and a first protective member 83 that protects the outer circumference of the light guide member 81. The illumination unit 80 has a holding member 85 that holds the distal portion of the light guide member 81 protruding from the distal portion of the first protective member 83 and a fixing unit 90 of the light guide member 81. In the state in which the first protective member 83 and the holding member 85 are separated from each other in the longitudinal axis direction of the fixing unit 90, the fixing unit 90 fixes the first protective member 83 and the holding member 85 to each other. Furthermore, the fixing unit 90 fixes the light guide member 81 to the first protective member 83 and the holding member 85 and fixes the light guide member 81 itself so that the light guide member 81 may be prevented from warping.

The light guide member 81 is optically connected to the light source portion 70 and the optical element 101 that is held by the holding member 85 and will be described hereinafter. The light guide member 81 guides the primary light emitted from the light source portion 70 to the optical element 101. The light guide member 81 has a column shape, e.g. a circular column shape. The light guide member 81 is disposed inside the operation portion 23 and the insertion portion 21, for example. The light guide member 81 can bend in a desired manner. The light guide member 81 is an optical fiber of a single line for example. The core diameter thereof is 50 μm, for example, and the numerical aperture NA is 0.2, for example. The optical fiber is a multi-mode optical fiber. The core diameter and the numerical aperture NA are not particularly limited. The light guide member 81 may be a bundle fiber. The optical fiber is formed of glass or plastic, for example. The optical fiber may be a multi-mode fiber of quartz, for example. The optical fiber is an elongated member that can bend by an external force. The optical fiber has a core that is not depicted in the diagram, a clad that covers the outer circumference of the core and is not depicted in the diagram, and a cover layer that covers the outer circumference of the clad and is not depicted in the diagram. For example, the cover layer improves the mechanical strength of the light guide member 81, such as the tensile resistance and the bending resistance, and prevents breaking of the light guide member 81. The cover layer is a resin such as nylon, acrylic, polyimide, or ethylene tetrafluoro ethylene (ETFE), for example. The cover layer covers a large part of the clad. For example, the large part of the clad represents the part that is not held by the holding member 85. In other words, in the holding member 85, the first protective member 83 and the cover layer are removed and the clad is exposed. The cover layer may extend to the holding member 85 to be inserted in a first hole 85a and cover the clad in the holding member 85. The cover layer may be disposed to the first protective member 83 and the clad may be exposed between the distal end of the first protective member 83 and the holding member 85. The cover layer may function as a different component from the optical fiber and the optical fiber may have the core and the clad. An emission end surface 81a of the light guide member 81 is a section perpendicular to the central axis of the core. The emission end surface 81a is formed by polishing or cleavage. The emission end surface 81a is disposed at the distal portion of the light guide member 81 and is optically connected to the optical element 101.

The first protective member 83 has a cylindrical shape, e.g. a circular cylindrical shape. When the light guide member 81 is inserted in the first protective member 83, the first protective member 83 covers the outer circumference of the light guide member 81. The outer circumferential surface of the light guide member 81 is the outer circumferential surface of the cover layer, for example. The inner circumferential surface of the first protective member 83 may be in tight contact with the outer circumferential surface of the light guide member 81. A gap that is not depicted in the diagram may be formed between the first protective member 83 and the light guide member 81. This gap may be filled with a component such as a resin that is not depicted in the diagram. The first protective member 83 covers the light guide member 81 in the insertion portion 21. Although not depicted in the diagram, the first protective member 83 may extend from the insertion portion 21 to the periphery of the light source portion 70 and cover the light guide member 81 in the operation portion 23.

Figure 3A:
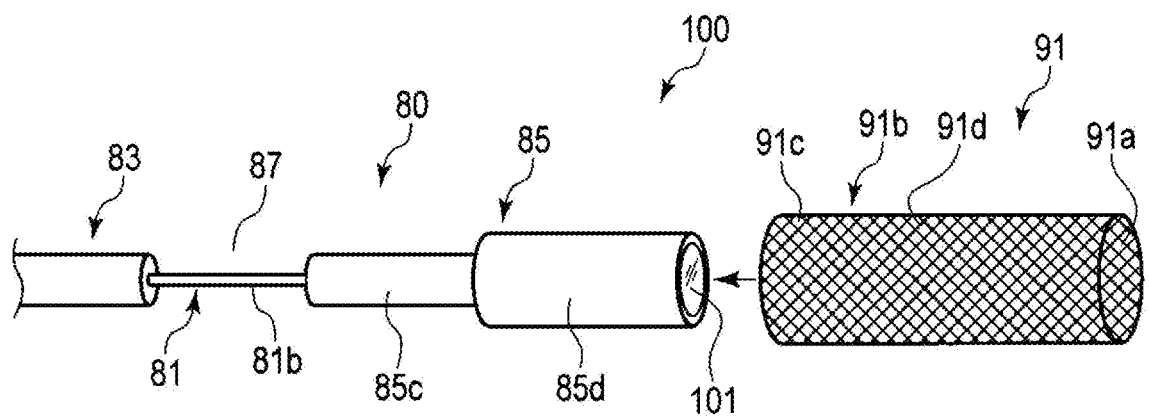
FIG. 3A is a diagram depicting one example of the process of covering of a first protective member, an exposed portion, and a holding member by a defining member as a reticular tube.
Figure 3B:
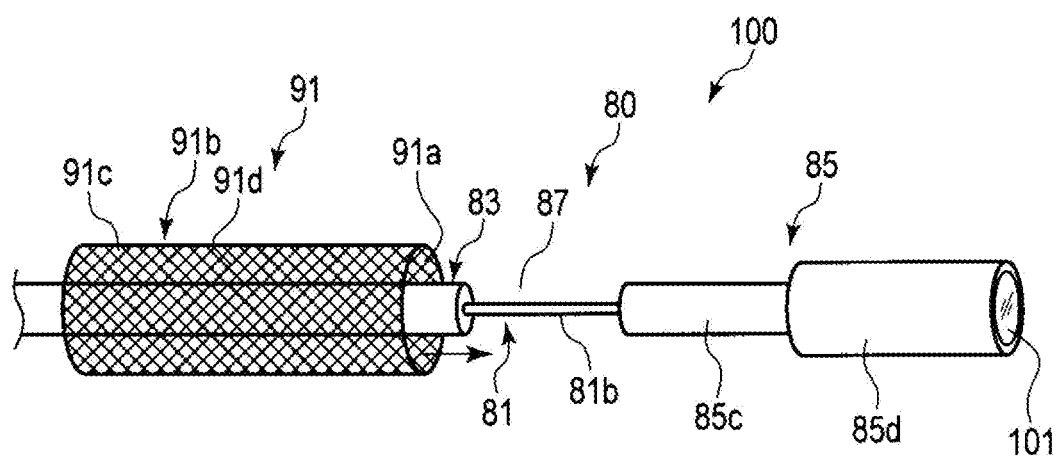
FIG. 3B is a diagram depicting one example of the process of covering of the first protective member, the exposed portion, and the holding member by the defining member as the reticular tube.

As depicted in FIG. 3A and FIG. 3B, in the state in which the distal portion of the light guide member 81 protrudes from the distal portion of the first protective member 83 toward the holding member 85 and the distal portion of the light guide member 81 is held by the holding member 85, the distal portion of the first protective member 83 is disposed separately from the holding member 85 in the longitudinal axis direction of the illumination unit 80. That is, in the longitudinal axis direction of the illumination unit 80, a space 87 is formed between the first protective member 83 and the holding member 85. The distal portion of the first protective member 83 may abut against the holding member 85.

The first protective member 83 is a resin, for example, and can bend in a desired manner. Similarly, to the cover layer, the first protective member 83 improves the mechanical strength of the light guide member 81, such as the tensile resistance and the bending resistance, and protects the light guide member 81 in order to prevent breaking of the light guide member 81.

As depicted in FIG. 2, in the present embodiment, the light guide member 81, the optical element 101, the fixing unit 90, and the first protective member 83 and the holding member 85 fixed to each other by the fixing unit 90 function as one illumination portion 100 of the illumination unit 80. The illumination portion 100 including the holding member 85 and so forth is disposed inside the distal portion of the insertion portion 21. Specifically, the illumination portion 100 is inserted in an illumination hole 21b disposed at a distal hard portion that is a distal holding portion 21a disposed inside the distal portion of the insertion portion 21. The inner diameter of the illumination hole 21b is substantially the same as the outer diameter of the illumination portion 100. The outer diameter of the illumination portion 100 represents the outer diameter of a thicker column portion 85d to be described hereinafter as the largest outer diameter of the holding member 85, for example. The illumination hole 21b has a circular column shape, for example.

The illumination portion 100 has the optical element 101 disposed in the holding member 85. The optical element 101 is irradiated with the primary light and converts optical characteristics of at least part of the applied primary light to generate the secondary light. Then, the optical element 101 emits the generated secondary light to the external as the illumination light.

For example, the optical element 101 has a truncated cone shape whose diameter increases from the rear side toward the front side. The optical element 101 has an incident surface portion 101a with e.g. a circular shape and an emission surface portion 101b with e.g. a circular shape. The emission end surface 81a of the light guide member 81 is optically connected to the incident surface portion 101a and the primary light is incident on the incident surface portion 101a. The emission surface portion 101b is larger than the incident surface portion 101a and emits the illumination light to the external of the illumination portion 100. The incident surface portion 101a has substantially the same size as the emission end surface 81a of the light guide member 81 or is larger than the emission end surface 81a. The optical element 101 has a circumferential surface that is disposed between the incident surface portion 101a and the emission surface portion 101b and has e.g. a curved surface shape. The circumferential surface is in tight contact with the inner circumferential surface of a second hole 85b to be described hereinafter in the holding member 85. A reflective member that is not depicted in the diagram may be disposed on the inner circumferential surface. The reflective member may be disposed across the whole circumference of the inner circumferential surface, for example. The reflective member is a film of a metal such as silver or aluminum, or the like, for example. The reflective member reflects the primary light or the secondary light that has traveled to the reflective member toward the front side.

The optical element 101 has an optical conversion component that is not depicted in the diagram and a containing component that contains the optical conversion component and is not depicted in the diagram. The optical conversion component is dispersed inside the containing component and is sealed by the containing component.

The optical conversion component has at least one of a wavelength conversion component that converts at least a partial wavelength of the primary light and is not depicted in the diagram and a diffusion component that diffuses at least part of the primary light and is not depicted in the diagram.

The wavelength conversion component absorbs the primary light and carries out wavelength conversion of the wavelength of the primary light to a wavelength longer than the wavelength of the primary light. The wavelength conversion component is a powder phosphor represented by YAG:Ce, for example. Such a wavelength conversion component absorbs blue light and emits yellow fluorescence. The generated fluorescence also travels in directions other than the front direction. Thus, it is also possible that the wavelength conversion component be referred to as a diffusion component in a broad sense.

The diffusion component enlarges the divergence angle of the primary light with which the diffusion component is irradiated light without changing the wavelength thereof to convert the primary light to diffused light with lowered coherence. The diffusion component is microparticles formed of a metal or metal compound, for example. Such a diffusion component is alumina, titanium oxide, barium sulfate, or the like, for example. The particle size of the diffusion component is several hundreds of nanometers to several tens of micrometers. The refractive index of the diffusion component is different from the refractive index of the containing component. For example, it is preferable that the refractive index of the diffusion component be higher than the refractive index of the containing component. This allows the diffusion component to improve the diffusibility of the primary light.

The containing component is formed of a component through which the primary light and the secondary light are transmitted. Such a containing component is a transparent silicone-based resin or transparent epoxy-based resin, for example. The containing component has a high transmittance with respect to the primary light and the secondary light. The containing component seals the component contained.

The holding member 85 holds the light guide member 81 and the optical element 101 in such a manner that the emission end surface 81a of the light guide member 81 and the optical element 101 are optically connected to each other. The holding member 85 is a metal, for example. The holding member 85 has the first hole 85a with which the light guide member 81 engages and the second hole 85b with which the optical element 101 engages. The first hole 85a and the second hole 85b are disposed along the longitudinal axis direction of the holding member 85 and are continuous with each other. The first hole 85a is disposed on the rear side and the second hole 85b is disposed on the front side. The first hole 85a is disposed in order for the holding member 85 to hold the light guide member 81, and functions as a holding hole. Therefore, the first hole 85a has a circular column shape. The light guide member 81 engages with the first hole 85a in the state in which the cover layer has been peeled off and the clad is exposed. The second hole 85b is disposed in order for the holding member 85 to hold the optical element 101, and functions as a holding hole. Therefore, the second hole 85b has a truncated cone shape whose diameter increases from the rear side toward the front side.

The holding member 85 has a thinner column portion 85c and the thicker column portion 85d thicker than the thinner column portion 85c. The thinner column portion 85c and the thicker column portion 85d have a column shape, e.g. a circular column shape. The thinner column portion 85c and the thicker column portion 85d are disposed along the longitudinal axis direction of the holding member 85 and are continuous with each other to be a monolithic object. The thinner column portion 85c may be attached to and detached from the thicker column portion 85d and be a separate body. The central axis of the thinner column portion 85c and the central axis of the thicker column portion 85d are disposed coaxially with each other. The thinner column portion 85c and the thicker column portion 85d are disposed rotationally symmetrically about the central axis of the core. The thinner column portion 85c is disposed on the rear side and the thicker column portion 85d is disposed on the front side. The thinner column portion 85c has the first hole 85a and the thicker column portion 85d has the first hole 85a and the second hole 85b. The first hole 85a is disposed on the same straight line in the thinner column portion 85c and the thicker column portion 85d. One step portion 85e is formed due to the difference in the size between the thinner column portion 85c and the thicker column portion 85d. When the step portion 85e is viewed from the front side, the step portion 85e is a ring-shaped flat plane, for example. The step portion 85e may have a tapered shape in such a manner that the diameter of the step portion 85e gradually increases from the rear side toward the front side.

The outer circumferential shape and size of the thinner column portion 85c are substantially the same as the outer circumferential shape and size of the first protective member 83. The thinner column portion 85c is disposed on the front side relative to the first protective member 83. Therefore, as depicted in FIG. 3A and FIG. 3B, the hereinbefore-described space 87 is disposed between the first protective member 83 and the thinner column portion 85c in the longitudinal axis direction of the illumination unit 80. It is preferable for the thinner column portion 85c to have a desired length. The outer circumferential surface of the thinner column portion 85c is disposed on the same plane as the outer circumferential surface of the first protective member 83.

As depicted in FIG. 2, when the thicker column portion 85d is inserted in the illumination hole 21b, the thicker column portion 85d engages with the illumination hole 21b. Therefore, the outer circumferential shape and size of the thicker column portion 85d are substantially the same as the inner circumferential shape and size of the illumination hole 21b.

As depicted in FIG. 2, the fixing unit 90 has a defining member 91 having a spatial region 91a in which the first protective member 83 and the holding member 85 are disposed in the state of being separated from each other in the longitudinal axis direction of the fixing unit 90. The fixing unit 90 has an adhesive 93 that is disposed in the spatial region 91a to bond at least part of the first protective member 83 and at least part of the holding member 85 to the defining member 91. Furthermore, the adhesive 93 bonds an exposed portion 81b that is part of the light guide member 81 to the defining member 91. The exposed portion 81b represents one part of the light guide member 81 that is disposed between the first protective member 83 and the holding member 85 in the spatial region 91a and is exposed from the first protective member 83 and the holding member 85. Therefore, the exposed portion 81b is disposed between the first protective member 83 and the holding member 85 in the longitudinal axis direction of the illumination unit 80 and is disposed in the space 87. In the exposed portion 81b, the cover layer, which is not depicted in the diagram, of the optical fiber covers the outer circumference of the clad. That is, the cover layer is exposed and the adhesive 93 bonds to the cover layer. In the exposed portion 81b, the cover layer may be removed and the clad may be exposed, and the adhesive 93 may bond to the clad. Although the exposed portion 81b is disposed in the present embodiment, the configuration does not need to be limited thereto. The first protective member 83 may extend to the holding member 85 and the light guide member 81 may be covered by the first protective member 83 and the holding member 85, and the exposed portion 81b may be eliminated. In this case, in the spatial region 91a, the adhesive 93 covers at least part of the first protective member 83 and at least part of the holding member 85 and bonds to the first protective member 83 and the holding member 85. Therefore, the adhesive 93 directly bonds to the light guide member 81 or indirectly bonds to the light guide member 81 with the intermediary of the first protective member 83 and the holding member 85.

As depicted in FIG. 2, FIG. 3A, FIG. 3B, FIG. 4A, FIG. 4B, and FIG. 4C, the defining member 91 has a cylindrical shape, e.g. a circular cylindrical shape. The defining member 91 has the spatial region 91a inside the defining member 91. In other words, the spatial region 91a represents the internal space of the defining member 91. For example, the distal portion of the first protective member 83, the thinner column portion 85c of the holding member 85, the space 87, and the exposed portion 81b are disposed in the spatial region 91a, which is the internal space of the defining member 91. The defining member 91 may be disposed across the whole of the illumination unit 80 along the longitudinal axis direction of the illumination unit 80 and cover the whole length of the protective member 83, the whole length of the holding member 85, the space 87, and the exposed portion 81b. It is preferable for the defining member 91 to cover the holding member 85 excluding the thicker column portion 85d in the holding member 85. As just described, it suffices for the defining member 91 to cover at least part of the first protective member 83, at least part of the holding member 85, and part of the light guide member 81 in the spatial region 91a. The part of the light guide member 81 is the exposed portion 81b of the light guide member 81 exposed from the protective member 83 and the holding member 85, for example.

Figure 4A:
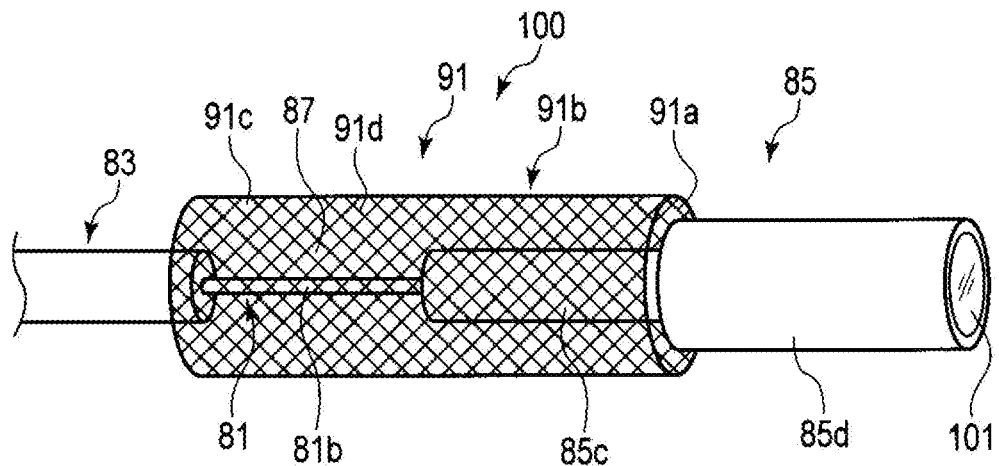
FIG. 4A is a diagram depicting the state in which the defining member as the reticular tube covers the first protective member, the exposed portion, and the holding member.
Figure 4B:
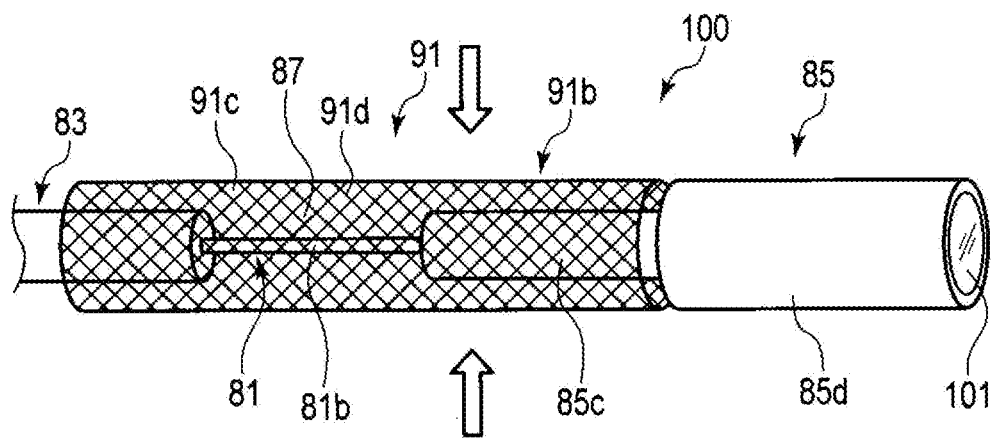
FIG. 4B is a diagram depicting the state in which the defining member depicted in FIG. 4A has extended and contracted.

As depicted in FIG. 4A and FIG. 4B, the defining member 91 can freely extend and contract in at least one of the longitudinal axis direction and the radial direction of the defining member 91. Therefore, based on extension and contraction in the longitudinal axis direction, the defining member 91 is allowed to adjust the length of covering of each of the distal portion of the first protective member 83 and the thinner column portion 85c. Furthermore, based on extension and contraction in the radial direction, the defining member 91 is allowed to be deformed to a shape along the outer circumferential shape of the distal portion of the first protective member 83 and the outer circumferential shape of the thinner column portion 85c, and can be in tight contact with the outer circumferential surface of each of the first protective member 83 and the thinner column portion 85c. In other words, the defining member 91 is allowed to adjust the transverse plane of the defining member 91 based on extension and contraction in the radial direction. The outer circumferential shape and size of the defining member 91 covering the first protective member 83 and the thinner column portion 85*c* become substantially the same as or smaller than the outer circumferential shape and size of the thicker column portion 85*d* due to extension and contraction of the defining member 91. For example, the defining member 91 contracts in the longitudinal axis direction when extending in the radial direction, and extends in the longitudinal axis direction when contracting in the radial direction.

The adhesive 93 is applied on the outer circumferential surface of the defining member 91, for example. The adhesive 93 enters the inside of the defining member 91, or spatial region 91*a*, from the outer circumferential surface through a specific region 91*b* to be described hereinafter in the defining member 91 based on the capillary phenomenon. Then, the spatial region 91*a* is filled with the adhesive 93. The adhesive 93 bonds to the first protective member 83, the holding member 85, the defining member 91, and the exposed portion 81*b* to bond the first protective member 83, the holding member 85, and the exposed portion 81*b* to the defining member 91. The spatial region 91*a* does not need to be filled with the adhesive 93 and the adhesive 93 may be disposed in at least part of the spatial region 91*a* as long as the adhesive 93 bonds the first protective member 83, the holding member 85, and the exposed portion 81*b* to the defining member 91.

In the present embodiment, the adhesive 93 wet-spreads along the outer circumferential surface of the defining member 91 due to the specific region 91*b* having gaps 91*c* and the surface tension of the adhesive 93. The adhesive 93 is disposed also in the gaps 91*c* although diagrammatic representation is avoided for clarification of diagrammatic representation. Furthermore, the adhesive 93 remains in the spatial region 91*a* due to the specific region 91*b* having the gaps 91*c* and the surface tension of the adhesive 93. In other words, the defining member 91 defines the bonding range of the adhesive 93 in at least one of the longitudinal axis direction and the radial direction of the defining member 91. Here, in the present embodiment, the length of the defining member 91 changes according to the disposing position of the first protective member 83 and the holding member 85 and the diameter of the defining member 91 changes according to the diameter of the first protective member 83 and the holding member 85. Such transformation is carried out based on extension and contraction of the defining member 91. Therefore, the defining member 91 defines the bonding range of the adhesive 93 corresponding to the disposing position of the first protective member 83 and the holding member 85 and the diameter of the first protective member 83 and the holding member 85. Specifically, the defining member 91 defines the bonding range of the adhesive 93 in such a manner that the adhesive 93 is disposed on the first protective member 83, the holding member 85, and the exposed portion 81*b*.

As described hereinbefore, the length of the defining member 91 is defined according to the disposing position of the first protective member 83 and the holding member 85 and the adhesive 93 remains in the spatial region 91*a* due to the specific region 91*b* having the gaps 91*c* and the surface tension of the adhesive 93. Therefore, in the longitudinal axis direction of the fixing unit 90, the adhesive 93 that wet-spreads falls within the spatial region 91*a* of the defining member 91 and the length of the adhesive 93 that wet-spreads becomes substantially the same as the length of the defining member 91 or longer than the length of the defining member 91. As just described, the defining member 91 defines the bonding range of the adhesive 93, in other words, the length of the adhesive 93 that wet-spreads, in further other words, the disposing position of the adhesive 93, in the longitudinal axis direction of the defining member 91.

Furthermore, the wet-spreading adhesive 93 spreads with an even thickness in the whole of the outer circumferential surface of the defining member 91 due to the specific region 91*b* having the gaps 91*c* and the surface tension of the adhesive 93. In other words, the thickness of the adhesive 93 disposed on the outer circumferential surface of the defining member 91 becomes even. That is, the outer circumferential shape and size of the adhesive 93 disposed on the outer circumferential surface of the defining member 91 are kept substantially the same as the outer circumferential shape and size of the defining member 91 due to the specific region 91*b* having the gaps 91*c* and the surface tension of the adhesive 93. As just described, the defining member 91 defines the outer circumferential shape and size of the adhesive 93 in such a manner that the outer circumferential shape and size of the adhesive 93 after curing become substantially the same as the outer circumferential shape and size of the defining member 91. In other words, the outer circumferential shape and size of the adhesive 93 applied along the outer circumference of the defining member 91 are defined to the outer circumferential shape and size of the defining member 91 by the defining member 91. The outer circumferential shape and size of the defining member 91 become substantially the same as or smaller than the outer circumferential shape and size of the thicker column portion 85*d* based on extension and contraction of the defining member 91. Therefore, the defining member 91 defines the outer circumferential shape and size of the adhesive 93 in such a manner that the outer circumferential shape and size of the adhesive 93 become substantially the same as or smaller than the outer circumferential shape and size of the thicker column portion 85*d*. As just described, the defining member 91 defines the bonding range of the adhesive 93, in other words, the thickness of the adhesive 93, in further other words, the disposing position of the adhesive 93, in the radial direction of the spatial region 91*a*.

The adhesive 93 is disposed also on the exposed portion 81*b*. At this time, the defining member 91 covers the exposed portion 81*b*, the space 87, and the adhesive 93 disposed on the exposed portion 81*b*. Therefore, the adhesive 93 disposed on the exposed portion 81*b* remains inside the defining member 91 due to the defining member 91. Furthermore, when the adhesive 93 is applied on the outer circumferential surface of the defining member 91 on the lateral side of the exposed portion 81*b* in order for the adhesive 93 to be disposed on the exposed portion 81*b*, the outer circumferential shape and size of the adhesive 93 are defined to the outer circumferential shape and size of the defining member 91 by the defining member 91.

The adhesive 93 disposed in the spatial region 91*a* bonds the first protective member 83 and the holding member 85 to the defining member 91. For example, the adhesive 93 fixes the distal portion of the defining member 91 to the thinner column portion 85*c* of the holding member 85 and fixes the proximal portion of the defining member 91 to the distal portion of the first protective member 83. At this time, the adhesive 93 covers the thinner column portion 85*c* and the distal portion of the first protective member 83, for example. Therefore, the adhesive 93 ensures the mechanical strength of the distal portion of the first protective member 83 and the thinner column portion 85c. The mechanical strength represents the tensile resistance and the bending resistance, for example.

Furthermore, the adhesive 93 fixes the first protective member 83 and the holding member 85 to each other. For this purpose, the adhesive 93 is disposed in the space 87, in other words, on the exposed portion 81b, for example. At this time, the adhesive 93 covers the exposed portion 81b, for example. Furthermore, the adhesive 93 fixes (bonds) the first protective member 83 and the holding member 85 to each other in the state of covering the exposed portion 81b. Moreover, the adhesive 93 disposed in the space 87, or exposed portion 81b, fixes the exposed portion 81b and the defining member 91 to each other and fixes (bonds) the exposed portion 81b and the first protective member 83 to each other and fixes (bonds) the exposed portion 81b and the holding member 85 to each other. In other words, the adhesive 93 whose bonding range is defined to the space 87, or exposed portion 81b, by the defining member 91 fixes the exposed portion 81b and the defining member 91 to each other and fixes (bonds) the exposed portion 81b and the first protective member 83 to each other and fixes (bonds) the exposed portion 81b and the holding member 85 to each other. In addition, the adhesive 93 that is disposed in the space 87, or exposed portion 81b, and covers the exposed portion 81b, in other words, the adhesive 93 whose bonding range is defined to the space 87, or exposed portion 81b, by the defining member 91, ensures the mechanical strength of the exposed portion 81b.

Because the adhesive 93 wet-spreads, in the defining member 91 filled with the adhesive 93, for example, the outer diameter of one part of the defining member 91 covering the exposed portion 81b does not become larger than the outer diameter of one part covering the thinner column portion 85c. That is, the fixing unit 90, or defining member 91, does not become thicker partly but keeps an even thickness across the whole length, and the thickness thereof becomes the same as the thicker column portion 85d or thinner than the thicker column portion 85d.

As just described, the adhesive 93 covers the exposed portion 81b and bonds to the first protective member 83, the holding member 85, the defining member 91, and the exposed portion 81b in the covering state. Furthermore, the adhesive 93 covers the exposed portion 81b in the spatial region 91a, and bonds at least part of the first protective member 83, at least part of the holding member 85, and the exposed portion 81b to the defining member 91 in such a manner that the adhesive 93 fixes the first protective member 83 and the holding member 85 to each other in the covering state and in such a manner that the adhesive 93 fixes the exposed portion 81b and the defining member 91 to each other in the covering state.

Figure 4C:
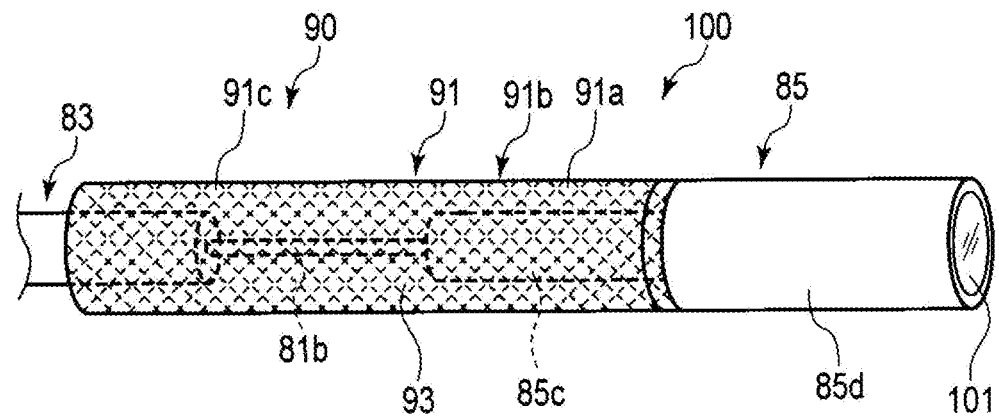
FIG. 4C is a diagram depicting the state in which the defining member is filled with an adhesive and the fixing unit fixes the first protective member and the holding member to each other.
Figure 5:
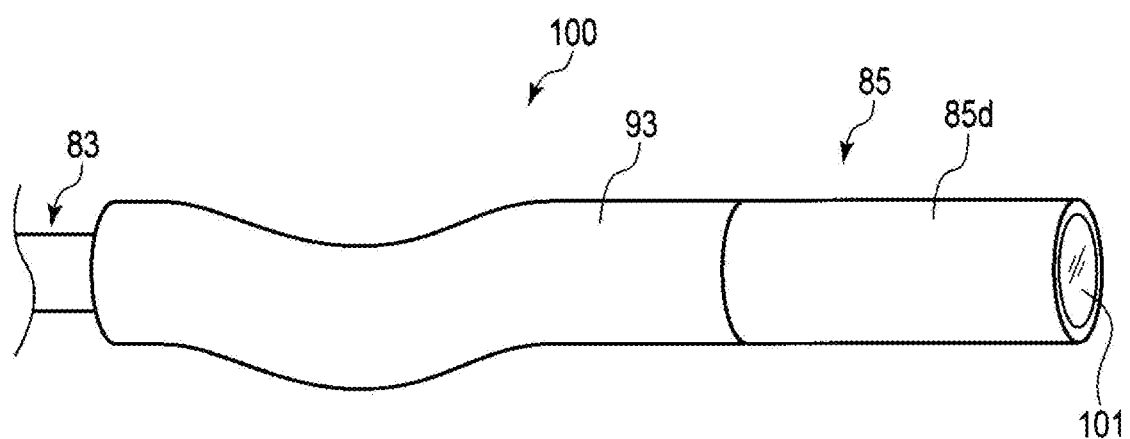
FIG. 5 is a diagram depicting that the adhesive has gotten distorted in the state in which the defining member is not disposed.

Here, suppose that the adhesive 93 is disposed on the exposed portion 81b in order to ensure the mechanical strength of the exposed portion 81b in the state in which the defining member 91 is not disposed differently from the present embodiment. In this case, engagement of the illumination portion 100 with the illumination hole 21b needs to be considered. Therefore, the outer circumferential shape and size of the adhesive 93 disposed on the outer circumference of the exposed portion 81b need to become substantially the same as or smaller than the outer circumferential shape and size of the thicker column portion 85d. However, in the state in which the defining member 91 is not disposed, due to the flow of the adhesive 93 itself, defining the bonding range of the adhesive 93 before curing becomes difficult, in other words, defining the length, outer circumferential shape, and size of the adhesive 93 before curing becomes difficult. Therefore, as depicted in FIG. 5, the shape of the adhesive 93 gets distorted before curing in some cases. Furthermore, although not depicted in the diagram, the adhesive 93 before curing occasionally flows to the outer circumferential surface of the thicker column portion 85d. When such distorted adhesive 93 or the adhesive 93 that has flowed to the outer circumferential surface of the thicker column portion 85d is cured, the bonding range of the adhesive 93 is not defined (controlled). For example, in some cases, it becomes impossible for the adhesive 93 to keep an even thickness across the whole of the adhesive 93, or the adhesive 93 is cured in the distorted state or the adhesive 93 becomes thicker than the thicker column portion 85d. Therefore, the illumination portion 100 cannot be inserted into the illumination hole 21b in some cases. However, in the present embodiment, as depicted in FIG. 2 and FIG. 4C, the bonding range of the adhesive 93 after curing is defined by the defining member 91 and the length, outer circumferential shape, and size of the adhesive 93 are defined to become substantially the same as the length, outer circumferential shape, and size of the defining member 91. Furthermore, the outer circumferential shape and size of the defining member 91 become substantially the same as or smaller than the outer circumferential shape and size of the thicker column portion 85d. Therefore, the defining member 91 defines the outer circumferential shape and size of the adhesive 93 that remains on the defining member 91 in such a manner that the outer circumferential shape and size of the adhesive 93 after curing become substantially the same as or smaller than the outer circumferential shape and size of the thicker column portion 85d. Accordingly, the illumination portion 100 is surely inserted into the illumination hole 21b.

As depicted in FIG. 2, FIG. 3A, and FIG. 3B, the defining member 91 has the specific region 91b that defines the bonding range of the adhesive 93 in the spatial region 91a. Furthermore, the specific region 91b causes the adhesive 93 to enter the spatial region 91a inside the defining member 91 from the outer circumferential surface of the defining member 91. The specific region 91b functions as the circumferential surface of the defining member 91, for example. Such a defining member 91 is a reticular tube, for example.

The defining member 91 as the reticular tube has the plural gaps 91c in the circumferential surface of the defining member 91. The gaps 91c penetrate the defining member 91 in the thickness direction of the defining member 91. The gaps 91c are inflow ports through which the adhesive 93 flows into the inside of the defining member 91, or spatial region 91a, from the outer circumferential surface of the defining member 91.

The defining member 91 as the reticular tube may be formed through braiding of plural thin wires 91d into a cylindrical shape. The defining member 91 as the reticular tube may be a component obtained by forming flat braid, or braided wire, formed of the plural woven wires 91d into a cylindrical shape. The wires 91d may be a metal such as copper, for example, or may be a resin. The gaps 91c are disposed among the wires 91d. Therefore, the specific region 91b has the gaps 91c disposed among the wires 91d in the reticular tube and the circumferential surface in which the gaps 91c are disposed.

Here, suppose that a defining member that is not depicted in the diagram is formed by braiding of one wire. The mechanical strength of the defining member 91 of the present embodiment is improved by e.g. flat braid compared with the mechanical strength of the defining member that is not depicted in the diagram. The mechanical strength represents the tensile resistance and the bending resistance, for example. Furthermore, compared with the defining member that is not depicted in the diagram, the defining member 91 of the present embodiment can protect the exposed portion 81*b* by the flat braid and prevent breaking of the exposed portion 81*b* by the flat braid.

In the defining member 91 as the reticular tube, based on the density of the wires 91*d* and the thickness of the wires 91*d*, the number and size of gaps 91*c* are adjusted and the entry rate of the adhesive 93 into the spatial region 91*a* is adjusted. Furthermore, when the adhesive 93 is applied on the outer circumferential surface of the defining member 91, the surface tension of the adhesive 93 is kept and the adhesive 93 is kept along the surface of the wires 91*d* based on the number and size of gaps 91*c*. In other words, the defining member 91 defines the bonding range of the adhesive 93 and the outer circumferential shape and size of the adhesive 93 based on the number and size of gaps 91*c*.

Although the defining member 91 is described as the reticular tube, the shape and configuration of the defining member 91 do not need to be limited thereto. It suffices that the defining member 91 have the spatial region 91*a* and the specific region 91*b* and the surface tension of the adhesive 93 be kept and the adhesive 93 be disposed in the spatial region 91*a*.

Figure 6A:
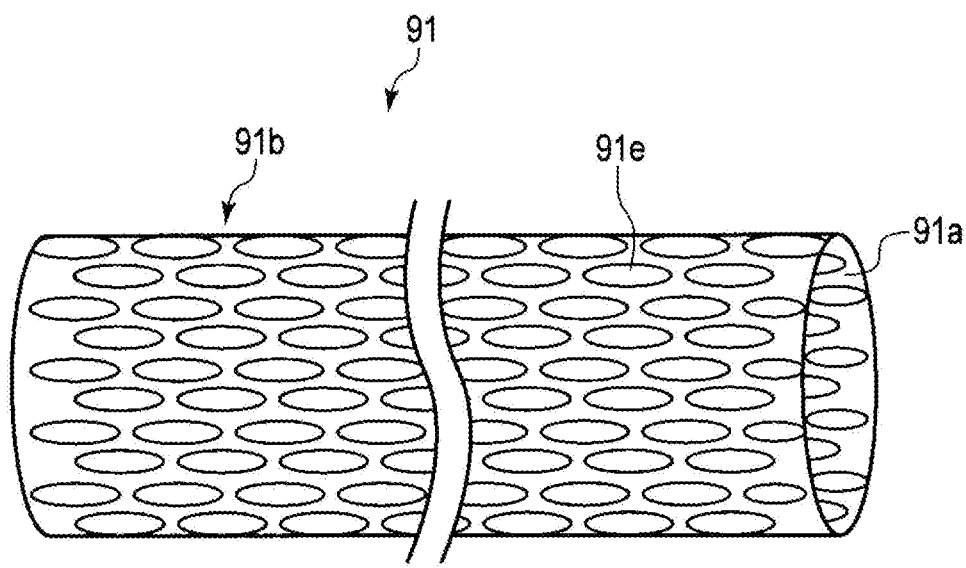
FIG. 6A is a diagram depicting one example of the defining member.

For example, as depicted in FIG. 6A, the defining member 91 may be a cylindrical member having through-holes 91*e* disposed in the circumferential surface of the defining member 91. The defining member 91 is a circular cylindrical member, for example. The through-holes 91*e* penetrate the defining member 91 in the thickness direction of the defining member 91. The adhesive 93 enters the inside of the defining member 91, or spatial region 91*a*, from the outer circumferential surface of the defining member 91 through the through-holes 91*e*, for example. The circumferential surface in which the through-holes 91*e* are disposed functions as the specific region 91*b*. The number and size of through-holes 91*e* are adjusted and the entry rate of the adhesive 93 into the spatial region 91*a* is adjusted. Furthermore, when the adhesive 93 is applied on the outer circumferential surface of the defining member 91, the defining member 91 defines the bonding range of the adhesive 93 and the outer circumferential shape and size of the adhesive 93 based on the number and size of through-holes 91*e*.

For example, the defining member 91 depicted in FIG. 6A may have a groove disposed in the inner circumferential surface of the defining member 91 although not depicted in the diagram. In this case, the adhesive 93 can spread through the groove.

Figure 6B:
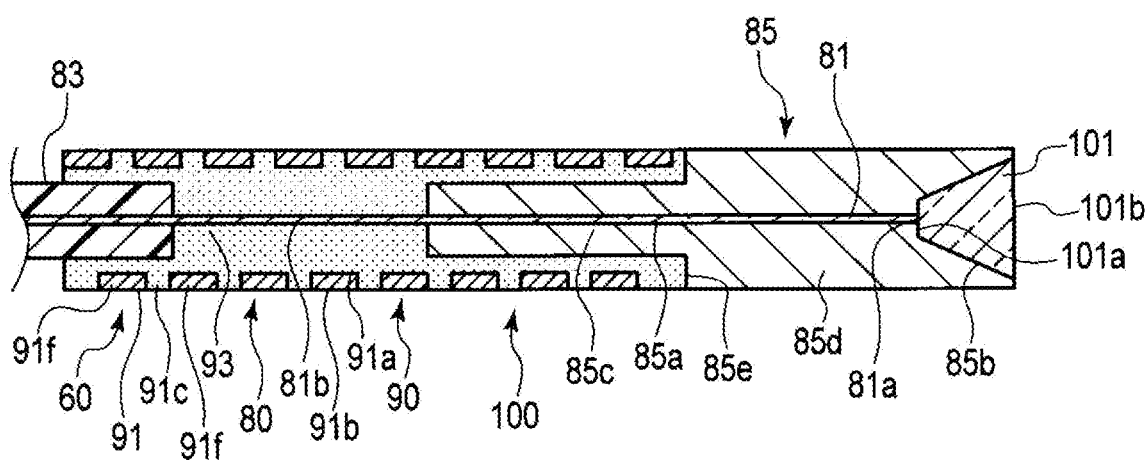
FIG. 6B is a diagram depicting one example of the defining member.

For example, as depicted in FIG. 6B, the defining member 91 may be a spiral tube disposed in a spiral manner in such a manner as to be wound around the distal portion of the protective member 83, the thinner column portion 85*c* of the holding member 85, and the exposed portion 81*b*. The defining member 91 as the spiral tube is formed into a substantially circular tube shape through shaping of a strip-shaped thin plate material into a spiral shape, for example. The thin plate material is a metal such as stainless steel or a resin, for example. The distal portion of the defining member 91 and the proximal portion of the defining member 91 are cut to be at substantially 90 degrees with respect to the central axis of the defining member 91. In the spiral tube, gaps 91*c* are disposed between winds 91*f* adjacent to each other in the longitudinal axis direction of the spiral tube. The gaps 91*c* are inflow ports through which the adhesive 93 flows into the inside of the defining member 91, or spatial region 91*a*, from the outer circumferential surface of the defining member 91. Therefore, the specific region 91*b* has, in the spiral tube, the gaps 91*c* disposed between the winds 91*f* adjacent to each other in the longitudinal axis direction of the spiral tube and the winds 91*f* forming the gaps 91*c*. The adhesive 93 is disposed in the gaps 91*c* and inside the defining member 91. Then, the adhesive 93 carries out bonding. The adhesive 93 may be disposed on the outer circumferential surface of the spiral tube. The thickness of the adhesive 93 disposed on the outer circumferential surface becomes even due to the specific region 91*b*.

The defining member 91 as the spiral tube may be disposed across the whole of the illumination unit 80 along the longitudinal axis direction of the illumination unit 80 in order to prevent collapse of the whole of the illumination unit 80 and local collapse of the defining member 91.

Although not depicted in the diagram, the defining member 91 as the spiral tube may be a component obtained by forming flat braid formed of the plural woven wires 91*d* into a spiral shape. Therefore, the gaps 91*c* are formed also in the spiral tube itself. In this case, the defining member 91 can freely extend and contract in at least one of the longitudinal axis direction and the radial direction of the defining member 91. The defining member 91 as the spiral tube may be a graphite sheet.

The defining member 91 may have thermal contractibility. When heat is applied to the defining member 91, the defining member 91 contracts due to the heat. Therefore, the defining member 91 that contracts due to the heat becomes capable of extending or contracting to a shape along the outer circumferential shape of the first protective member 83 and the outer circumferential shape of the thinner column portion 85*c* and can be in tight contact with the outer circumferential surfaces of the first protective member 83 and the thinner column portion 85*c*. This heat represents heat generated from the optical element 101 when the optical element 101 generates the secondary light, for example. Alternatively, when the primary light travels in the light guide member 81, part of the primary light is converted to heat in the light guide member 81. This heat is transmitted from the light guide member 81 to the first protective member 83, the holding member 85, and the adhesive 93 and is released from the first protective member 83, the holding member 85, and the adhesive 93. The released heat is transmitted to the defining member 91 and the defining member 91 contracts due to the heat.

The adhesive 93 may be an epoxy-based adhesive or silicone-based adhesive, for example. The adhesive 93 is cured by ultraviolet (UV) light, for example.

Here, with reference to FIG. 3A, FIG. 3B, FIG. 4A, FIG. 4B, and FIG. 4C, attaching of the defining member 91 as a reticular tube to the first protective member 83, the holding member 85, and the exposed portion 81*b* will be simply described.

As depicted in FIG. 3A, the light guide member 81 is protected by the first protective member 83. In the state in which the optical element 101 engages with the second hole 85*b* in advance, the distal portion of the light guide member 81 engages with the first hole 85*a* in such a manner that the light guide member 81 is optically connected to the optical element 101, and the holding member 85 holds the distal portion of the light guide member 81 and the optical element 101. Thereby, the exposed portion 81*b* is formed. Thereafter, for example, the defining member 91 travels from the thicker column portion 85*d* toward the first protective member 83 in the state in which the diameter of the defining member 91 is larger than the diameter of the thicker column portion 85*d*. Then, as depicted in FIG. 4A, the defining member 91 covers the distal portion of the first protective member 83, the thinner column portion 85*c* of the holding member 85, the space 87, and the exposed portion 81*b*.

As depicted in FIG. 3B, the defining member 91 may cover the first protective member 83 in the state in which the light guide member 81 is protected by the first protective member 83. The defining member 91 travels from the first protective member 83 toward the thicker column portion 85*d*. Then, as depicted in FIG. 4A, the defining member 91 may cover the distal portion of the first protective member 83, the thinner column portion 85*c* of the holding member 85, the space 87, and the exposed portion 81*b*.

As depicted in FIG. 4B, the defining member 91 extends in the longitudinal axis direction of the defining member 91, for example. Therefore, the range covered by the defining member 91 regarding each of the first protective member 83 and the thinner column portion 85*c* is adjusted. Due to this extension, the defining member 91 contracts in the radial direction of the defining member 91, for example. Due to this contraction, the outer circumferential shape and size of the distal portion of the defining member 91 become substantially the same as the outer circumferential shape and size of the thinner column portion 85*c* and the distal portion of the defining member 91 comes in tight contact with the outer circumferential surface of the thinner column portion 85*c*. Furthermore, due to this contraction, the outer circumferential shape and size of the proximal portion of the defining member 91 become substantially the same as the outer circumferential shape and size of the distal portion of the first protective member 83 and the proximal portion of the defining member 91 comes in tight contact with the outer circumferential surface of the distal portion of the first protective member 83. The defining member 91 certainly covers the whole of the space 87 disposed between the first protective member 83 and the thinner column portion 85*c*. It suffices for the defining member 91 to cover the distal portion of the first protective member 83 and the defining member 91 may cover the whole of the first protective member 83.

The adhesive 93 is applied on the outer circumferential surface of the defining member 91 and enters the inside of the defining member 91, or spatial region 91*a*, through the gaps 91*c*. As depicted in FIG. 4C, the spatial region 91*a* is filled with the adhesive 93. The adhesive 93 remains in the spatial region 91*a* due to the specific region 91*b* having the gaps 91*c* and the surface tension of the adhesive 93. In other words, the bonding range of the adhesive 93 in at least one of the longitudinal axis direction and the radial direction of the defining member 91 is defined by the defining member 91 so that the adhesive 93 may be disposed on the first protective member 83, the holding member 85, and the exposed portion 81*b*. Due to this, the adhesive 93 falls within the spatial region 91*a* of the defining member 91 and the length of the adhesive 93 that remains in the defining member 91 becomes substantially the same as the length of the defining member 91 or shorter than the length of the defining member 91. Furthermore, the outer circumferential shape and size of the adhesive 93 that remains in the defining member 91 are kept substantially the same as the outer circumferential shape and size of the defining member 91.

In this state, the adhesive 93 is irradiated with UV light to be cured. This causes the adhesive 93 to bond to the first protective member 83, the holding member 85, the defining member 91, and the exposed portion 81*b* and bond the first protective member 83, the holding member 85, and the exposed portion 81*b* to the defining member 91. The adhesive 93 fixes the proximal portion of the defining member 91 to the distal portion of the first protective member 83 and fixes the distal portion of the defining member 91 to the thinner column portion 85*c* of the holding member 85. The adhesive 93 whose bonding range is defined to the distal portion of the first protective member 83 and the thinner column portion 85*c* by the defining member 91 ensures the mechanical strength of the distal portion of the first protective member 83 and the thinner column portion 85*c*. Furthermore, the adhesive 93 whose bonding range is defined to the space 87, or exposed portion 81*b*, by the defining member 91 fixes the first protective member 83 and the holding member 85 to each other and fixes the exposed portion 81*b* and the defining member 91 to each other and fixes the exposed portion 81*b* and the first protective member 83 to each other and fixes the exposed portion 81*b* and the holding member 85 to each other. The optical connection between the light guide member 81 and the optical element 101 is kept by the fixing between the exposed portion 81*b* and the holding member 85. The adhesive 93 whose bonding range is defined to the space 87, or exposed portion 81*b*, by the defining member 91 ensures the mechanical strength of the exposed portion 81*b*.

In the state in which the strength is ensured, the thickness of the fixing unit 90, or defining member 91, becomes substantially the same as the thicker column portion 85*d* or thinner than the thicker column portion 85*d*. Therefore, the illumination portion 100 is inserted into the illumination hole 21*b* without being affected by the adhesive 93 and engages with the illumination hole 21*b*.

In the present embodiment, the defining member 91 has the spatial region 91*a* in which the first protective member 83, the holding member 85, and the exposed portion 81*b* are disposed. In other words, the defining member 91 covers the first protective member 83, the holding member 85, and the exposed portion 81*b*. The adhesive 93 is disposed in the spatial region 91*a* and bonds the first protective member 83 and the holding member 85 to the defining member 91. The defining member 91 defines the bonding range of the adhesive 93 in at least one of the longitudinal axis direction and the radial direction of the defining member 91. Therefore, in the present embodiment, by the defining member 91, the length, outer circumferential shape, and size of the adhesive 93 disposed on the defining member 91 can be defined and the strength of the illumination portion 100, which is a unit including the adhesive 93, can be ensured.

In the present embodiment, the adhesive 93 can be caused to easily enter the spatial region 91*a* (inside) of the defining member 91 by the specific region 91*b*. In the present embodiment, the adhesive 93 can be wet-spread along the outer circumferential surface of the defining member 91 by the specific region 91*b* and the surface tension of the adhesive 93. When the adhesive 93 wet-spreads, the adhesive 93 can be made to remain in the spatial region 91*a* by the specific region 91*b* and the surface tension of the adhesive 93. Based on the length of the defining member 91 having the specific region 91*b*, the bonding range of the adhesive 93, in other words, the length of the adhesive 93, can be defined in the longitudinal axis direction of the defining member 91. Furthermore, the thickness of the adhesive 93 disposed on the outer circumferential surface of the defining member 91 can be made even by the specific region 91*b* and the surface tension of the adhesive 93. Moreover, the outer circumferential shape and size of the adhesive 93 disposed on the outer circumferential surface of the defining member 91 can be kept substantially the same as the outer circumferential shape and size of the defining member 91 by the specific region 91*b* having the gaps 91*c* or the through-holes 91*e* and the surface tension of the adhesive 93. In the present embodiment, the surface tension of the adhesive 93 can be improved by the specific region 91*b*. Furthermore, the outer circumferential shape and size of the adhesive 93 can be surely defined to the outer circumferential shape and size of the defining member 91 by the improved surface tension. The outer circumferential shape and size of the defining member 91 become substantially the same as the outer circumferential shape and size of the thinner column portion 85*c* and become substantially the same as the outer circumferential shape and size of the distal portion of the first protective member 83 and become substantially the same as or smaller than the outer circumferential shape and size of the thicker column portion 85*d*. Moreover, the fixing unit 90, or defining member 91, keeps an even thickness across the whole length and the thickness thereof becomes the same as the thicker column portion 85*d* or thinner than the thicker column portion 85*d*. Therefore, variation in the outer circumferential shape and size of the illumination portion 100 can be suppressed and the outer circumferential shape of the illumination portion 100 can be controlled. In addition, the adhesive 93 does not get caught in the illumination hole 21*b* and the illumination portion 100 can be inserted into the illumination hole 21*b*. The inner circumferential shape and size of the illumination hole 21*b* are defined in advance at the time of design of the endoscope 20 and the illumination hole 21*b* cannot be deformed when the illumination portion 100 is inserted into the illumination hole 21*b*. In the present embodiment, because the outer circumferential shape and size of the adhesive 93 after curing are defined, the outer diameter of the illumination portion 100 always becomes even and the evenness is kept every time the illumination portion 100 is assembled. Therefore, the illumination portion 100 can be surely inserted into the illumination hole 21*b*. The bonding range of the adhesive 93 and the outer circumferential shape and size of the adhesive 93 can be defined based on the number and size of gaps 91*c* or through-holes 91*e*.

In the present embodiment, by the adhesive 93, the first protective member 83 and the holding member 85 can be fixed (bonded) to each other and the exposed portion 81*b* and the defining member 91 can be fixed (bonded) to each other. In addition, the exposed portion 81*b* and the first protective member 83 can be fixed (bonded) to each other and the exposed portion 81*b* and the holding member 85 can be fixed (bonded) to each other. Because the adhesive 93 covers the first protective member 83 and the thinner column portion 85*c*, the mechanical strength of the first protective member 83 and the thinner column portion 85*c* can be ensured. Furthermore, because the adhesive 93 covers the exposed portion 81*b*, the mechanical strength of the exposed portion 81*b* can be ensured. The illumination portion 100 is disposed inside the insertion portion 21 that bends due to an external force. Therefore, the illumination portion 100 for which the mechanical strength is ensured can withstand an external pressure associated with the bending.

The spatial region 91*a* is filled with the adhesive 93. Therefore, the mechanical strength of the first protective member 83, the thinner column portion 85*c*, and the exposed portion 81*b* can be surely ensured. Furthermore, the illumination portion 100 for which the mechanical strength is ensured can surely withstand the external pressure associated with the bending. For the adhesive 93, the outer circumferential shape and size of the adhesive 93 applied along the outer circumference of the defining member 91 are defined to the outer circumferential shape and size of the defining member 91 by the specific region 91*b*. This can surely define the outer circumferential shape and size of the adhesive 93 to the outer circumferential shape and size of the defining member 91. Moreover, variation in the outer circumferential shape and size of the illumination portion 100 can be suppressed and the outer circumferential shape of the illumination portion 100 can be surely controlled. Therefore, the adhesive 93 after curing does not get caught in the illumination hole 21*b* and the illumination portion 100 can be surely inserted into the illumination hole 21*b*. Furthermore, in the present embodiment, the outer circumferential shape and size of the adhesive 93 are defined and the mechanical strength of the illumination portion 100 is ensured. In addition, in the illumination portion 100, the circular column shape is always kept. Accordingly, the illumination portion 100 can be smoothly inserted into the illumination hole 21*b* with a circular column shape without folding the exposed portion 81*b* and the illumination portion 100. Moreover, warping and breaking of the exposed portion 81*b* associated with an external force and bending of the insertion portion 21 can be prevented by the adhesive 93.

In the present embodiment, the defining member 91 can extend and contract in at least one of the longitudinal axis direction and the radial direction. Therefore, when the defining member 91 extends and contracts in the longitudinal axis direction, the length of covering of each of the distal portion of the first protective member 83 and the thinner column portion 85*c* by the defining member 91 is allowed to be adjusted. The defining member 91 can be deformed to a shape along the outer circumferential shape of the distal portion of the first protective member 83 and the outer circumferential shape of the thinner column portion 85*c* through extension and contraction in the radial direction. When the defining member 91 is fixed to the first protective member 83 and the thinner column portion 85*c* by the adhesive 93, the defining member 91 can be fixed to the components to which the defining member 91 is fixed (first protective member 83 and thinner column portion 85*c*) in the state in which the shape of the defining member 91 is along the outer circumferential shapes of the components to which the defining member 91 is fixed.

In the present embodiment, the defining member 91 is a reticular tube and the specific region 91*b* has the gaps 91*c* disposed among the wires 91*d* in the reticular tube. Alternatively, the defining member 91 is a spiral tube and the specific region 91*b* has the gaps 91*c* disposed between the winds 91*f* adjacent to each other in the longitudinal axis direction of the spiral tube. Therefore, the surface tension of the adhesive 93 can be kept and the wet-spreading of the adhesive 93 can be promoted. Furthermore, the spatial region 91*a* can be surely filled with the adhesive 93 and the mechanical strength of the illumination portion 100 can be ensured, so that breaking of the exposed portion 81*b* can be surely prevented. Furthermore, in the reticular tube, the number and size of gaps 91*c* can be controlled and the surface tension can be controlled, so that the bonding range of the adhesive 93 and the outer circumferential shape and size of the adhesive 93 can be controlled.

In the present embodiment, the defining member 91 covers the thinner column portion 85*c* in the holding member 85. However, there is no need to limit the configuration thereto. It suffices for the defining member 91 to cover a part having substantially the same outer circumferential shape and size as the outer circumferential shape and size of the first protective member 83 in the holding member 85. There is also no need for this part to be adjacent to the space 87. It is preferable for the outer circumferential surface of this part to have a desired length because the defining member 91 bonds to this part. Furthermore, the defining member 91 may cover the part adjacent to the space 87 in the holding member 85.

Modification Example 1 of First Embodiment

Figure 7A:
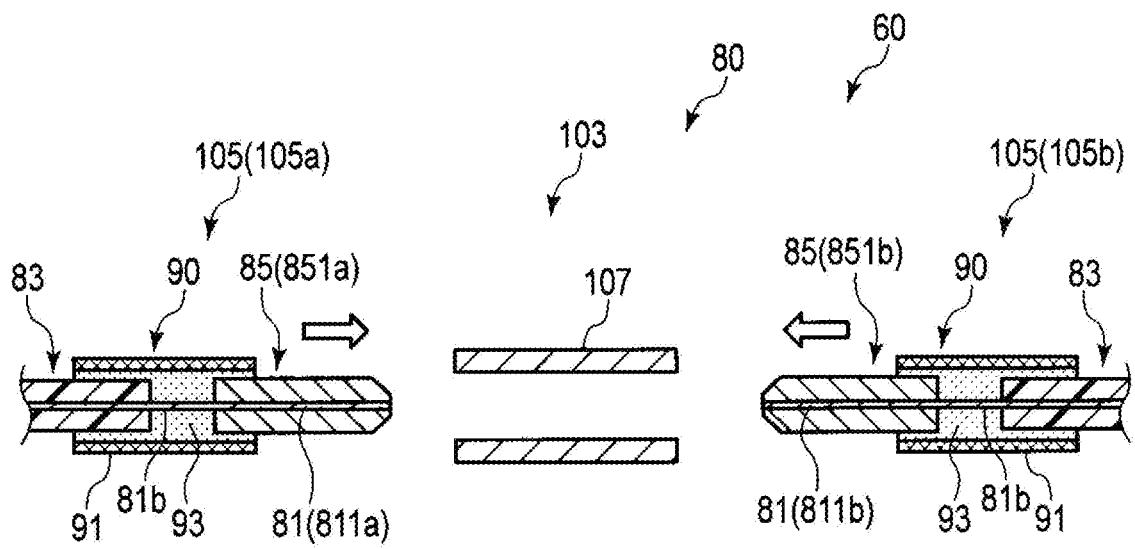
FIG. 7A is a diagram that depicts modification example 1 of the first embodiment and depicts that the fixing units are applied to an optical connector in the illumination apparatus.
Figure 7B:
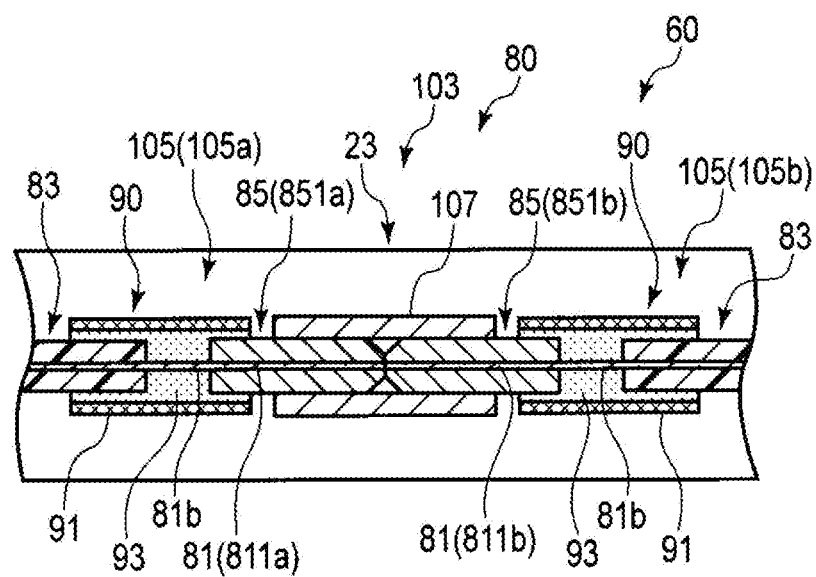
FIG. 7B is a diagram depicting that the optical connector depicted in FIG. 7A is disposed in an operation portion.

With reference to FIG. 7A and FIG. 7B, only a different configuration from the first embodiment will be described hereinafter.

In the present modification example, the holding member 85 functions as a ferrule that holds only the light guide member 81. Furthermore, the fixing unit 90 and the first protective member 83 and the holding member 85 fixed to each other by the fixing unit 90 are disposed in an optical connector 103 of the illumination unit 80 and function as a holding unit 105 that holds the light guide member 81.

As depicted in FIG. 7B, the optical connector 103 including the holding units 105 is disposed in the operation portion 23 of the endoscope 20 joined to the proximal portion of the insertion portion 21, for example. As depicted in FIG. 7A and FIG. 7B, the optical connector 103 has a cylindrical metal sleeve 107 and a pair of holding units 105 whose respective holding members 85 are inserted from both ends of the sleeve 107. The pair of holding units 105 optically connect the light guide members 81 held by a respective one of the holding units 105 to each other by the insertion. The first protective members 83 and the defining members 91 are disposed outside the sleeve 107.

Hereinafter, for convenience, the pair of holding units 105 will be referred to as first and second holding units 105*a* and 105*b*, respectively, and the holding members 85 of the first and second holding units 105*a* and 105*b* will be referred to as first and second holding members 851*a* and 851*b*. Furthermore, the light guide members 81 held by a respective one of the first and second holding members 851*a* and 851*b* will be referred to as first and second light guide members 811*a* and 811*b*. The configurations, shapes, and sizes of the first and second holding units 105*a* and 105*b* are substantially the same as each other.

The sleeve 107 has an inner diameter substantially the same as the outer diameter of the first and second holding units 105*a* and 105*b*. The sleeve 107 is a split sleeve, for example. The sleeve 107 presses the first and second holding units 105*a* and 105*b* in the radial direction of the sleeve 107 to fix them in such a manner that the first and second light guide members 811*a* and 811*b* are optically connected to each other.

The first holding unit 105*a* is disposed on the side of the light source portion 70, for example, and the second holding unit 105*b* is disposed on the side of the insertion portion 21, for example. The first light guide member 811*a* is optically connected to the light source portion 70 and the second light guide member 811*b* is optically connected to the illumination portion 100.

The first holding member 851*a* is tapered toward the sleeve 107 and has a projected shape. The tapered distal surface side of the first holding member 851*a* is inserted into the sleeve 107 and the proximal portion of the first holding member 851*a* is disposed outside the sleeve 107. The first holding member 851*a* holds the first light guide member 811*a* in such a manner that the distal surface of the first holding member 851*a* and an end surface of the first light guide member 811*a* are disposed on the same plane. The distal surface of the first holding member 851*a* and the end surface of the first light guide member 811*a* are polished. Although the description is made about the first holding unit 105*a*, this is the same also about the second holding member 851*b* of the second holding unit 105*b*.

The optical connector 103 may have a pressing mechanism that is not depicted in the diagram and presses the first holding unit 105*a* and the second holding unit 105*b* toward each other in the longitudinal axis direction of the optical connector 103. The pressing mechanism has a spring component, for example. This causes surface-abutting of the first holding member 851*a* and the second holding member 851*b* against each other. The surface-abutting represents abutting of the whole of the distal surface of the first holding member 851*a* against the whole of the tip surface of the second holding member 851*b*, for example.

As just described, the fixing unit 90 can be applied to the illumination portion 100 or the optical connector 103 in the illumination apparatus 60. In other words, the fixing unit 90 is a fixing unit for optical use used for an optical component such as the illumination portion 100 or the optical connector 103.

Modification Example 2 of First Embodiment

Figure 8A:
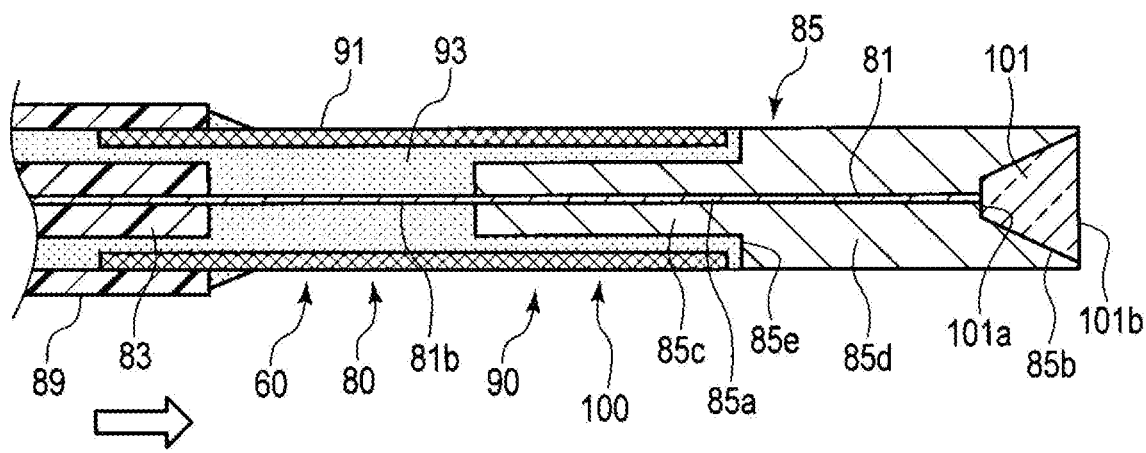
FIG. 8A is a diagram that depicts modification example 2 of the first embodiment and depicts the state in which a second protective member extends from the first protective member to the proximal portion of the defining member.
Figure 8B:
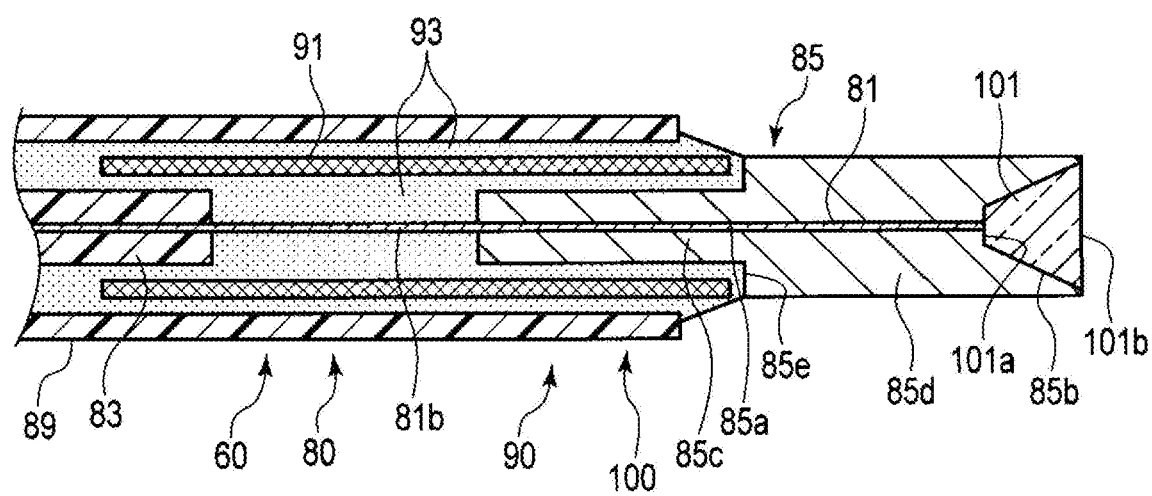
FIG. 8B is a diagram that depicts modification example 2 of the first embodiment and depicts the state in which the second protective member extends from the first protective member to the distal portion of the defining member.
Figure 8C:
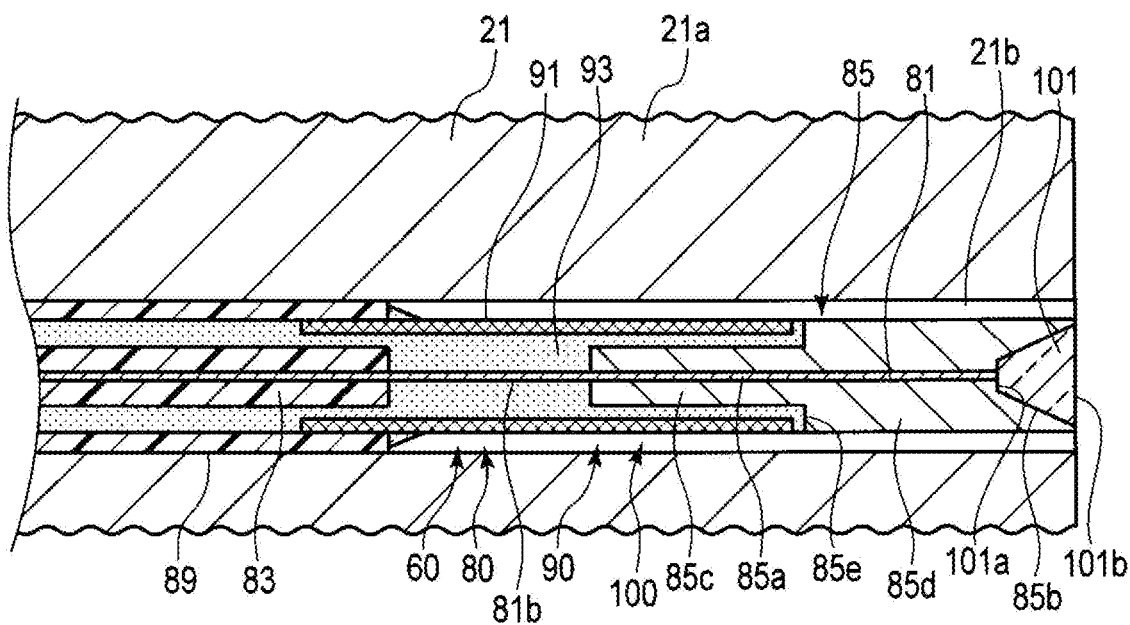
FIG. 8C is a diagram depicting that the illumination portion depicted in FIG. 8A is disposed in an illumination hole.

With reference to FIG. 8A, FIG. 8B, and FIG. 8C, only a different configuration from the first embodiment will be described hereinafter.

The illumination unit 80 further has a second protective member 89 that protects the outer circumference of the first protective member 83. The second protective member 89 has a cylindrical shape, e.g. a circular cylindrical shape. When the first protective member 83 is inserted in the second protective member 89, the second protective member 89 covers the outer circumference of the first protective member 83. A gap is formed between the first protective member 83 and the second protective member 89. The second protective member 89 is a resin, for example, and can bend in a desired manner. The second protective member 89 protects the light guide member 81 with the intermediary of the first protective member 83 in order to improve the mechanical strength of the light guide member 81 such as the tensile resistance and the bending resistance and prevent breaking of the light guide member 81 similarly to the first protective member 83.

The second protective member 89 covers the defining member 91. At this time, the second protective member 89 may extend from the first protective member 83 to the proximal portion of the defining member 91 as depicted in FIG. 8A or extend from the first protective member 83 to the distal portion of the defining member 91 as depicted in FIG. 8B.

The inside of the defining member 91 is filled with the adhesive 93. Next, the adhesive 93 is applied on the outer circumferential surface of the defining member 91 and the outer circumferential surface of the first protective member 83. Thereafter, the second protective member 89 covers the first protective member 83 and the defining member 91. The adhesive 93 is disposed inside the second protective member 89 or the inside of the second protective member 89 is filled with the adhesive 93. Furthermore, the adhesive 93 fixes (bonds) the second protective member 89 to the first protective member 83 and the defining member 91.

Suppose that the second protective member 89 covers the first protective member 83 and the defining member 91 after the inside of the defining member 91 has been already filled with the adhesive 93. The adhesive 93 is applied on the outer circumferential surface of the defining member 91 and enters between the outer circumferential surface of the defining member 91 and the inner circumferential surface of the second protective member 89 from the outer circumferential surface of the defining member 91 based on the capillary phenomenon. Due to this, the adhesive 93 is disposed inside the second protective member 89 or the inside of the second protective member 89 is filled with the adhesive 93. Furthermore, the adhesive 93 fixes (bonds) the second protective member 89 to the first protective member 83 and the defining member 91.

As depicted in FIG. 8C, when the illumination portion 100 engages with the illumination hole 21b, the adhesive 93 does not get caught in the illumination hole 21b and the illumination portion 100 can surely engage with the illumination hole 21b.

Second Embodiment

Figure 9:
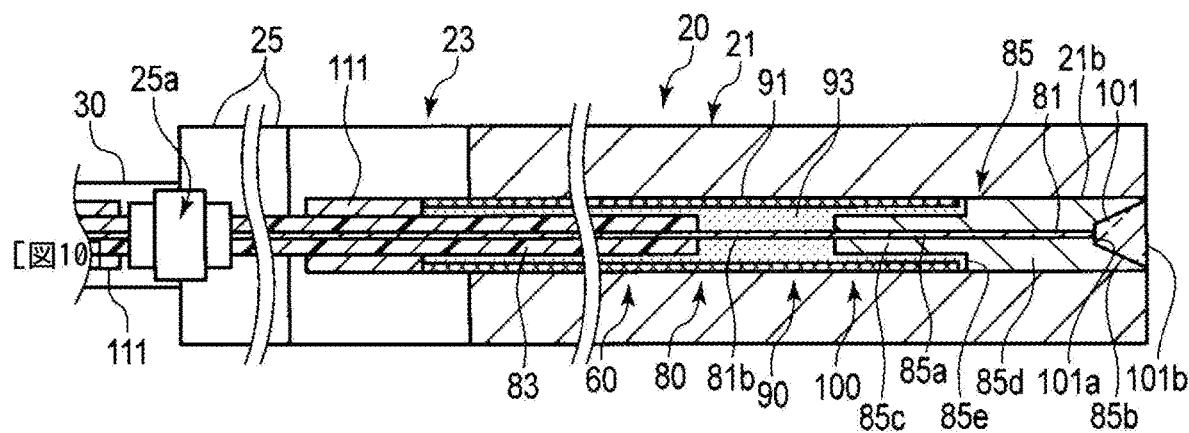
FIG. 9 is a diagram depicting a fixing unit according to a second embodiment.

A second embodiment of the disclosed technology will be described hereinafter with reference to FIG. 9. In the present embodiment, only a different configuration from the first embodiment will be described.

A defining member 91 has thermal conductivity. The defining member 91 is a metal such copper or a graphite sheet, for example. The defining member 91 is disposed from the distal portion of the insertion portion 21 to the operation portion 23.

The defining member 91 is thermally connected to the light guide member 81, the first protective member 83, the holding member 85, and the adhesive 93 and is thermally connected to the optical element 101 via the holding member 85. When generating the secondary light, the optical element 101 generates heat. Furthermore, when the primary light travels in the light guide member 81, part of the primary light is converted to heat in the light guide member 81. This heat is transferred from the light guide member 81 to the first protective member 83, the holding member 85, and the adhesive 93 and is released from the first protective member 83, the holding member 85, and the adhesive 93. The released heat is transferred to the defining member 91. The defining member 91 transfers, to the proximal portion of the defining member 91, the heat transferred from each of the light guide member 81, the first protective member 83, the holding member 85, and the adhesive 93. That is, the defining member 91 transfers the heat to the side of the proximal portion of the insertion portion 21.

The proximal portion of the defining member 91 may be thermally connected to a heat release member 111 disposed in the operation portion 23. The defining member 91 transfers the heat to the heat release member 111 and the heat release member 111 releases the transferred heat. The heat release member 111 is a component having high thermal conductivity. The heat release member 111 is a copper plate, for example. The heat release member 111 may function as a casing portion of the operation portion 23.

The defining member 91 may be disposed from the distal portion of the insertion portion 21 to apparatus to which the endoscope 20 is connected. This apparatus is the control apparatus 30, for example. Furthermore, the heat release member 111 may be disposed in the control apparatus 30 and function as a casing portion of the control apparatus 30.

In the present embodiment, the defining member 91 has thermal conductivity and transfers, to the rear side, heat transferred from each of the light guide member 81, the first protective member 83, the holding member 85, the adhesive 93, and the optical element 101. Therefore, a rise in the temperature of the illumination unit 80 can be suppressed. Furthermore, when the optical element 101 generates the secondary light, temperature quenching of the optical element 101 can be reduced and the light amount of illumination light can be kept. When the optical element 101 generates the secondary light, a large amount of heat is generated. Because the defining member 91 can transfer this heat to the operation portion 23, a rise in the temperature of the distal end of the insertion portion 21 can be suppressed.

The configuration of the present embodiment can be applied also to modification examples 1 and 2 of the first embodiment.

Third Embodiment

Figure 10:
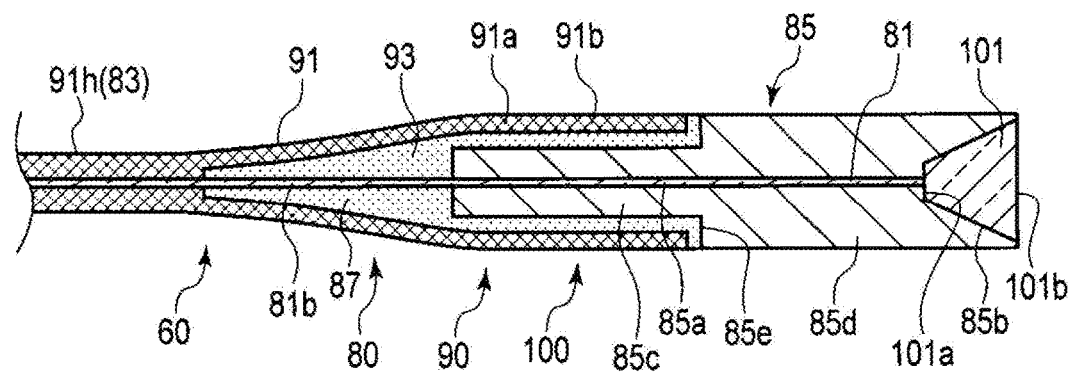
FIG. 10 is a diagram depicting a fixing unit according to a third embodiment.

A third embodiment of the disclosed technology will be described hereinafter with reference to FIG. 10. In the present embodiment, only a different configuration from the first embodiment will be described.

In the present embodiment, a defining member 91 has the first protective member 83. One part of the defining member 91 other than the part that covers the exposed portion 81b and the holding member 85 is a protective part 91h that functions as the first protective member 83. The protective part 91h may be in tight contact with the light guide member 81, for example. The defining member 91 is a reticular tube, for example, similarly to the first embodiment.

For example, the defining member 91 extends and spreads in the radial direction and the longitudinal axis direction of the defining member 91 to cover the thinner column portion 85c. For example, the defining member 91 contracts in the radial direction of the defining member 91 and is along to the outer circumference of the thinner column portion 85c. The spatial region 91a is filled with the adhesive 93 through the specific region 91b. In the present embodiment, the spatial region 91a may be defined as only the inside of the one part of the defining member 91 covering the exposed portion 81b and the holding member 85. In this case, the adhesive 93 only fixes the defining member 91 to the exposed portion 81b and the thinner column portion 85c and improves the mechanical strength of the exposed portion 81b and the thinner column portion 85c. The spatial region 91a may be disposed across the whole length of the defining member 91. In this case, the adhesive 93 may be further disposed on the protective part 91h or the protective part 91h may be filled with the adhesive 93. Furthermore, the adhesive 93 may bond the protective part 91h to the light guide member 81.

In the present embodiment, the first protective member 83 can be made unnecessary and thus the number of components of the illumination unit 80 can be reduced. Furthermore, in the present embodiment, it suffices to only fill the inside of the one part of the defining member 91 covering the exposed portion 81b and the holding member 85 with the adhesive 93 and fix the defining member 91 to the exposed portion 81b and the thinner column portion 85c by the adhesive 93. Therefore, in the present embodiment, the assembly step of the illumination portion 100 can be reduced.

Fourth Embodiment

A fourth embodiment of the disclosed technology will be described hereinafter with reference to FIG. 11A and FIG. 11B. In the present embodiment, only a different configuration from the first embodiment will be described.

A defining member 91 has a wettability improvement surface (hereinafter, referred to as improvement surface 91g) that improves the wettability of the adhesive 93. For example, the improvement surface 91g represents the circumferential surface of the defining member 91 for which any one of surface cleaning, plasma cleaning, etching by acid or alkali, polishing, and primer treatment by a silane compound has been carried out.

In the present embodiment, by the improvement surface 91g, the wettability of the adhesive 93 can be improved and the adhesive 93 can be made to remain on the circumferential surface. Therefore, in the present embodiment, the size and number of gaps 91c or through-holes 91e disposed in the circumferential surface can be reduced and the configuration of the defining member 91 can be simplified.

For example, the improvement surface 91g is disposed in the whole of the inner circumferential surface of the defining member 91 or the whole of the outer circumferential surface of the defining member 91. The improvement surface 91g may be disposed in at least part of the inner circumferential surface or may be disposed in at least part of the outer circumferential surface. The improvement surface 91g may be disposed in at least one of the inner circumferential surface of the defining member 91 and the outer circumferential surface of the defining member 91, for example. As just described, it suffices for the improvement surface 91g to be disposed in at least part of at least one of the inner circumferential surface of the defining member 91 and the outer circumferential surface of the defining member 91.

Figure 11A:
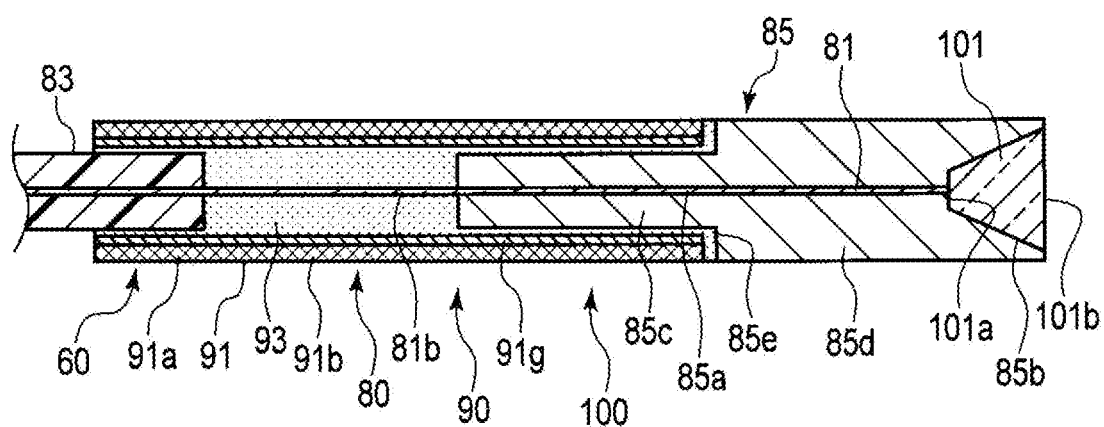
FIG. 11A is a diagram depicting one example of a fixing unit according to a fourth embodiment.

Suppose that the improvement surface 91g is disposed in the inner circumferential surface as depicted in FIG. 11A. In this case, in the present embodiment, the adhesive 93 applied on the outer circumferential surface can be made to rapidly enter the inside of the defining member 91 and be wet-spread on the inner circumferential surface. Furthermore, in the present embodiment, unnecessary running-over of the adhesive 93 to the outer circumferential surface of the defining member 91 can be suppressed.

Figure 11B:
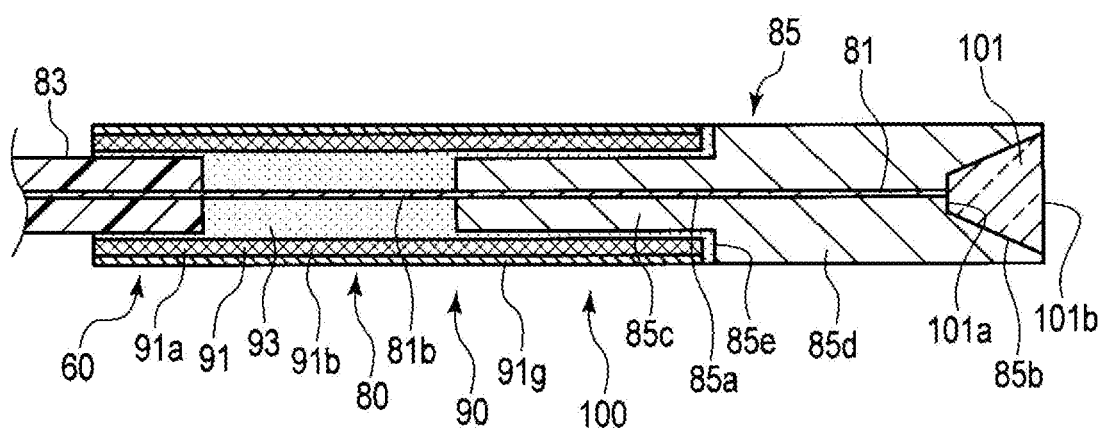
FIG. 11B is a diagram depicting one example of the fixing unit according to the fourth embodiment.

Suppose that the improvement surface 91g is disposed in the outer circumferential surface as depicted in FIG. 11B. In this case, in the present embodiment, the adhesive 93 applied on the outer circumferential surface can be wet-spread on the outer circumferential surface. Furthermore, in the present embodiment, the thickness of the adhesive 93 disposed on the outer circumferential surface of the defining member 91 can be made more even.

In sum, one aspect of the disclosed technology is directed to a fixing unit of a light guide member. The fixing unit is attaching the light guide member to a protective member that protects outer circumference of the light guide member that guides primary light and a holding member that holds an end portion of the light guide member that protrudes from the protective member. The fixing unit comprises a defining member forming a spatial region in which the protective member and the holding member are encapsulated separately from one another in a longitudinal axis direction of the fixing unit. An adhesive that is applied in the spatial region to bond at least part of the protective member and at least part of the holding member to the defining member. The defining member includes a specific region that defines a bonding range of the adhesive in the spatial region in at least one of a longitudinal axis direction and a radial direction of the defining member.

The defining member has the spatial region inside the defining member and covers, in the spatial region, the at least part of the protective member, the at least part of the holding member, and part of the light guide member. The defining member has a cylindrical shape and the specific region configured to receive the adhesive in the spatial region inside the cylindrical shape from an outer circumferential surface of the cylindrical shape. The part of the light guide member is an exposed portion of the light guide member exposed from the protective member and the holding member. The adhesive covers the exposed portion in the spatial region. The spatial region is filled with the adhesive. An outer circumferential shape and size of the adhesive being inside of an outer circumferential shape and size of the defining member by the specific region. The defining member extends and contracts in at least one of the longitudinal axis direction and the radial direction of the defining member and extends and contracts to a shape along an outer circumferential shape of the protective member and an outer circumferential shape of the holding member. The defining member is a reticular tube in which a plurality of wires are braided into a cylindrical shape or is a spiral tube disposed in a spiral manner in such a manner as to be wound around the protective member. The holding member, and the exposed portion, and the specific region has gaps disposed among the wires in the reticular tube or has gaps disposed between winds adjacent to each other in a longitudinal axis direction of the spiral tube. The defining member has a wettability improvement surface that improves wettability of the adhesive. The wettability improvement surface is disposed in at least part of an inner circumferential surface of the defining member or the outer circumferential surface of the defining member. The defining member is made from material having thermal conductivity and is thermally connected to the respective light guide member, the protective member, the holding member, and the adhesive so as to transfer heat from each of the light guide member, the protective member, the holding member, and the adhesive.

The holding member includes an optical element that is irradiated with the primary light and converts an optical characteristic of at least part of the primary light for emitting a secondary light to surrounding as illumination light. The holding member is disposed inside a distal portion of an insertion portion of an endoscope. The defining member is disposed from the distal portion of the insertion portion to an operation portion joined to a proximal portion of the insertion portion or apparatus to which the endoscope is connected. The defining member transfers, to a side of the proximal portion of the insertion portion, the heat generated from the primary light guided by the light guide member or the heat generated from the optical element when the optical element generates the secondary light, or the defining member is thermally connected to a heat release member disposed in the operation portion or disposed in the apparatus and transfers the heat to the heat release member. The defining member has the protective member. The respective fixing unit, the protective member and the holding member are attached to one another that function as one illumination portion of an illumination unit or are disposed in an optical connector of the illumination unit that functions as one holding unit that holds the light guide member. The illumination portion has an optical element that is disposed in the holding member, is irradiated with the primary light and converts an optical characteristic of at least part of the primary light with which the optical element is irradiated so as to generate secondary light and emit the generated secondary light to surrounding as illumination light, and the illumination portion is inserted in an illumination hole disposed in a distal holding portion disposed inside a distal portion of an endoscope insertion portion, and the holding unit is disposed in an operation portion of an endoscope joined to the endoscope insertion portion.

Another aspect of the disclosed technology is directed to an illumination apparatus comprises a light source that emits primary light. An illumination unit that converts an optical characteristic of at least part of the primary light emitted from the light source to generate secondary light and emit the generated secondary light to external as illumination light. The illumination unit has a light guide member that guides the primary light emitted from the light source. A protective member that protects outer circumference of the light guide member. A holding member that holds an end portion of the light guide member that protrudes from the protective member. A fixing unit of the light guide member as described herein before.

The fixing unit and the protective member and the holding member are attached to one another to function as one illumination portion of the illumination unit. The illumination portion includes an optical element that is disposed in the holding member, is irradiated with the primary light, and converts an optical characteristic of at least part of the primary light for emitting a secondary light to surrounding as the illumination light. The holding member holds the light guide member and the optical element in such a manner that the light guide member and the optical element are optically connected to one another. The illumination portion is inserted in an illumination hole disposed in a distal holding portion disposed inside a distal portion of an endoscope insertion portion. The respective fixing unit, the protective member and the holding member are attached to one another disposed in an optical connector of the illumination unit functions as one holding unit that holds the light guide member. The holding member functioning as a ferrule and the optical connector includes a sleeve with a cylindrical shape. A pair of holding units that each include a respective one of the holding members inserted from both ends of the sleeve and optically connect the light guide members each held by a respective one of the holding units to each other by the insertion. The optical connector is disposed in an operation portion of an endoscope joined to an endoscope insertion portion.

A further aspect of the disclosed technology is directed to an endoscope comprises having an illumination apparatus. The illumination apparatus comprises a light source that emits primary light. An illumination unit that converts an optical characteristic of at least part of the primary light emitted from the light source to generate secondary light and emit the generated secondary light to external as illumination light. The illumination unit has a light guide member that guides the primary light emitted from the light source. A protective member that protects outer circumference of the light guide member. A holding member that holds an end portion of the light guide member that protrudes from the protective member. A fixing unit as described herein before fixes the protective member and the holding member to each other in a state in which the protective member and the holding member are separated from each other in a longitudinal axis direction of the fixing unit.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

The disclosed technology is not limited to the embodiments themselves described hereinbefore and can be embodied with a constituent element modified within such a range as not to depart from the gist thereof at the stage of implementation. Furthermore, various inventions can be formed based on appropriate combinations of plural constituent elements disclosed in the embodiments described hereinbefore.

What is claimed is:

1. A holding unit comprising:
a light guide that guides primary light;
a protective tube for covering an outer circumference of a first portion of the light guide;
a holding tube that holds a second portion of the light guide that protrudes from the protective tube, the first portion of the light guide being offset relative to the second portion of the light guide in a longitudinal axis direction of the light guide;
a defining sleeve defining a spatial region in which at least a first portion of the protective tube and at least a second portion of the holding tube are disposed separately from one another in the longitudinal axis direction of the light guide; and an adhesive applied in the spatial region to bond at least the first portion of the protective tube and at least the second portion of the holding tube to the defining sleeve, wherein the defining sleeve includes a specific region that defines a bonding range of the adhesive in the spatial region in at least one of the longitudinal axis direction and a radial direction of the defining sleeve.

2. The holding unit of claim 1, wherein the defining sleeve has the spatial region inside the defining sleeve and covers, within the spatial region, at least the first portion of the protective tube, at least the second portion of the holding tube, and a third portion of the light guide.

3. The holding unit of claim 2, wherein the defining sleeve has a cylindrical shape, and the specific region is configured to receive the adhesive in the spatial region inside the cylindrical shape from an outer circumferential surface of the cylindrical shape.

4. The holding unit of claim 3, wherein
the third portion of the light guide is an exposed portion of the light guide exposed between the first portion of the protective tube and the second portion of the holding tube, and
the adhesive covers the exposed portion in the spatial region.

5. The holding unit of claim 4, wherein the spatial region is filled with the adhesive, an outer circumferential shape and size of the adhesive being inside of an outer circumferential shape and size of the defining sleeve.

6. The holding unit of claim 5, wherein the defining sleeve is configured to extend and contract in at least one of the longitudinal axis direction and the radial direction of the defining sleeve and extend and contract to a shape along an outer circumferential shape of the protective tube and an outer circumferential shape of the holding tube.

7. The holding unit of claim 6, wherein
the defining sleeve is a reticular tube in which a plurality of wires are braided into a cylindrical shape or is a spiral tube disposed in a spiral manner in such a manner as to be wound around the protective tube, the holding tube, and the exposed portion, and
the specific region has gaps disposed among the wires in the reticular tube or has gaps disposed between winds adjacent to each other in a longitudinal axis direction of the spiral tube.

8. The holding unit of claim 5, wherein the defining sleeve has a wettability improvement surface that increases wettability with the adhesive.

9. The holding unit of claim 8, wherein the wettability improvement surface is disposed in at least part of an inner circumferential surface of the defining sleeve or the outer circumferential surface of the defining sleeve.

10. The holding unit of claim 4, wherein the defining sleeve is made from a material having thermal conductivity and is thermally connected to the respective light guide, the protective tube, the holding tube, and the adhesive so as to transfer heat from each of the light guide, the protective tube, the holding tube, and the adhesive.

11. The holding unit of claim 10, wherein
the holding tube includes an optical element that is irradiated with the primary light and converts an optical characteristic of at least part of the primary light for emitting a secondary light as illumination light and wherein the holding tube is configured to be disposed inside a distal portion of an insertion portion of an endoscope, the defining sleeve is configured to be disposed from the distal portion of the insertion portion to an operation portion joined to a proximal portion of the insertion portion or an apparatus to which the endoscope is connected, and the defining sleeve transfers, to a side of the proximal portion of the insertion portion, the heat generated from the primary light guided by the light guide member or the heat generated from the optical element when the optical element generates the secondary light, or the defining sleeve is thermally connected to a heat release material disposed in the operation portion or disposed in the apparatus and transfers the heat to the heat release material.

12. The holding unit of claim 4,
further comprising an optical element that is disposed in the holding tube, is irradiated with the primary light and converts an optical characteristic of at least part of the primary light with which the optical element is irradiated so as to generate secondary light and emit the generated secondary light as illumination light, and the illumination portion is configured to be inserted in an illumination hole disposed in a distal holding portion disposed inside a distal portion of an endoscope insertion portion, and
the holding unit is configured to be disposed in an operation portion of an endoscope joined to the endoscope insertion portion.

13. An illumination apparatus comprising:
the holding unit of claim 1;
a light source that emits the primary light to the light guide; and
an illumination unit optical element that converts an optical characteristic of at least part of the primary light emitted from the light source to generate secondary light and emit the generated secondary light as illumination light.

14. The illumination apparatus of claim 13, wherein
the optical element is disposed in the holding tube, and
the holding tube holds the light guide and the optical element such that the light guide and the optical element are optically connected to one another.

15. The illumination apparatus of claim 14, wherein the illumination unit is configured to be inserted in an illumination hole disposed in a distal holding portion disposed inside a distal portion of an endoscope insertion portion.

16. An endoscope comprising:
the holding unit of claim 1;
a light source that emits the primary light to the light guide; and
an illumination unit optical element that converts an optical characteristic of at least part of the primary light emitted from the light source to generate secondary light and emit the generated secondary light as illumination light.

17. An illumination apparatus comprising:
the holding unit of claim 1; and
a light source that emits the primary light to the light guide.

18. The illumination apparatus comprising:
the holding unit of claim 1; and an optical element that converts an optical characteristic of at least part of the primary light to generate secondary light and emit the generated secondary light as illumination light.

19. A light guide coupler comprising:
a first light guide;
a second light guide;
a first holding unit comprising:
  a first tube for covering an outer circumference of a first portion of the first light guide;
  a second tube that holds an end of the first light guide that protrudes from the first tube;
  a first sleeve defining a first spatial region in which at least a first end of the first tube and at least a first end of the second tube are disposed separately from one another in a longitudinal axis direction of the first light guide, the first end of the first tube and the first end of the second tube being opposed to each other, the end of the first light guide being flush with a second end of the second tube; and
  a first adhesive applied in the first spatial region to bond at least the first end of the first tube and at least the first end of the second tube to the first sleeve;
a second holding unit comprising:
  a third tube for covering an outer circumference of a first portion of the second light guide;
  a fourth tube that holds an end of the second light guide that protrudes from the third tube;
  a second sleeve defining a second spatial region in which at least a first end of the third tube and at least a first end of the fourth tube are disposed separately from one another in a longitudinal axis direction of the second light guide, the first end of the third tube and the first end of the fourth tube being opposed to each other, the end of the second light guide being flush with a second end of the fourth tube; and
  a second adhesive applied in the second spatial region to bond at least the first end of the third tube and at least the first end of the fourth tube to the second sleeve; and
a coupler sleeve coupling the second end of the second tube to the second end of the fourth tube such that the end of the first light guide is in optical communication with the end of the second light guide.

* * * * *